United States Patent
Langdale et al.

(10) Patent No.: US 10,687,874 B2
(45) Date of Patent: Jun. 23, 2020

(54) PROXIMAL HUMERAL STABILIZATION SYSTEM

(71) Applicant: GLOBUS MEDICAL, INC., Audubon, PA (US)

(72) Inventors: Evan Langdale, Philadelphia, PA (US); David R. Jansen, Glenmoore, PA (US); Malcolm Smith, Chelsea, MA (US); Andrew Davison, Downingtown, PA (US); Stephanie Wolfe, Hatfield, PA (US); Henry C. Rutledge, Lansdale, PA (US); Thomas Shinn, Pottstown, PA (US); Barclay Davis, Glenmoore, PA (US)

(73) Assignee: Globus Medical, Inc, Audubon, PA (US)

( * ) Notice: Subject to any disclaimer, the term of this patent is extended or adjusted under 35 U.S.C. 154(b) by 187 days.

(21) Appl. No.: 15/238,767

(22) Filed: Aug. 17, 2016

(65) Prior Publication Data

US 2017/0056081 A1    Mar. 2, 2017

(51) Int. Cl.
*A61B 17/80*    (2006.01)
*A61B 17/72*    (2006.01)
*A61B 17/17*    (2006.01)

(52) U.S. Cl.
CPC ...... *A61B 17/8061* (2013.01); *A61B 17/1728* (2013.01); *A61B 17/72* (2013.01);
(Continued)

(58) Field of Classification Search
CPC ............ A61B 17/68; A61B 17/72–748; A61B 17/80–8095
See application file for complete search history.

(56) References Cited

U.S. PATENT DOCUMENTS

| | | |
|---|---|---|
| 1,105,105 A | 7/1914 | Sherman |
| 2,486,303 A | 10/1949 | Longfellow |

(Continued)

FOREIGN PATENT DOCUMENTS

| | | |
|---|---|---|
| CN | 201987653 U | 9/2011 |
| CN | 202313691 U | 7/2012 |

(Continued)

OTHER PUBLICATIONS

Boraiah, S. et al., The surgical approach, its vascular implications and the importance of medial calcar support in maintaining fracture reduction in locked plating of proximal humerus fractures—A review, 2008, PB Journal of Orthopedics, vol. 10, No. 1, pp. 14-20.

*Primary Examiner* — Nicholas J Plionis

(57) ABSTRACT

Devices, systems, and methods for bone stabilization, especially proximal humeral stabilization. The stabilization system may include a bone plate having an elongated portion extending along a longitudinal axis and an enlarged head portion extending from the elongated portion. The stabilization system may include an intramedullary nail having an upper portion and a lower portion extending from the upper portion, the upper portion and the lower portion including a plurality of holes. A plurality of fasteners may be configured to extend through one or more of the plurality of through holes in the bone plate and/or one or more of the plurality of holes in the intramedullary nail and into the bone. The plate and nail may each be used alone or in combination together to stabilize a fracture in a long bone, such as a humerus.

17 Claims, 30 Drawing Sheets

(52) U.S. Cl.
CPC ............ *A61B 17/725* (2013.01); *A61B 17/80* (2013.01); *A61B 17/8014* (2013.01); *A61B 17/8052* (2013.01); *A61B 17/8057* (2013.01)

(56) References Cited

U.S. PATENT DOCUMENTS

| | | | |
|---|---|---|---|
| 3,716,050 A | 2/1973 | Johnston | |
| 4,493,317 A | 1/1985 | Klaue | |
| 4,524,765 A | 6/1985 | de Zbikowski | |
| 4,651,724 A | 3/1987 | Berentey et al. | |
| 4,683,878 A | 8/1987 | Carter | |
| 4,781,183 A | 11/1988 | Casey et al. | |
| 4,867,144 A | 9/1989 | Karas et al. | |
| 5,002,544 A | 3/1991 | Klaue et al. | |
| 5,041,114 A | 8/1991 | Chapman et al. | |
| 5,151,103 A | 9/1992 | Tepic et al. | |
| 5,259,398 A | 11/1993 | Vrespa | |
| 5,356,410 A * | 10/1994 | Pennig .................. | A61B 17/744 |
| | | | 606/281 |
| 5,364,399 A | 11/1994 | Lowery et al. | |
| 5,372,598 A | 12/1994 | Luhr et al. | |
| 5,423,826 A | 6/1995 | Coates et al. | |
| 5,601,553 A | 2/1997 | Trebing et al. | |
| 5,676,667 A | 10/1997 | Hausman | |
| 5,709,686 A | 1/1998 | Talos et al. | |
| 5,718,704 A | 2/1998 | Medoff | |
| 5,746,742 A | 5/1998 | Runciman et al. | |
| 5,785,712 A | 7/1998 | Runciman et al. | |
| 5,938,664 A | 8/1999 | Winquist et al. | |
| 6,001,099 A | 12/1999 | Huebner | |
| 6,096,040 A | 8/2000 | Enser | |
| 6,152,927 A | 11/2000 | Farris et al. | |
| 6,206,881 B1 | 3/2001 | Frigg et al. | |
| 6,283,969 B1 | 9/2001 | Grusin et al. | |
| 6,309,393 B1 | 10/2001 | Tepic et al. | |
| 6,322,562 B1 | 11/2001 | Wolter | |
| 6,364,882 B1 | 4/2002 | Orbay | |
| 6,533,786 B1 | 3/2003 | Needham et al. | |
| 6,623,486 B1 | 9/2003 | Weaver et al. | |
| 6,669,700 B1 | 12/2003 | Farris et al. | |
| 6,669,701 B2 | 12/2003 | Steiner et al. | |
| 6,712,820 B2 | 3/2004 | Orbay | |
| 6,719,759 B2 | 4/2004 | Wagner et al. | |
| 6,730,091 B1 | 5/2004 | Pfefferle et al. | |
| 6,866,665 B2 | 3/2005 | Orbay | |
| 6,955,677 B2 | 10/2005 | Dahners | |
| 6,974,461 B1 | 12/2005 | Wolter | |
| 7,001,387 B2 | 2/2006 | Farris et al. | |
| 7,063,701 B2 | 6/2006 | Michelson | |
| 7,128,744 B2 | 10/2006 | Weaver et al. | |
| 7,137,987 B2 | 11/2006 | Patterson et al. | |
| 7,153,309 B2 | 12/2006 | Huebner et al. | |
| 7,179,260 B2 | 2/2007 | Gerlach et al. | |
| 7,250,053 B2 | 7/2007 | Orbay | |
| 7,294,130 B2 | 11/2007 | Orbay | |
| 7,322,963 B2 | 1/2008 | Harris | |
| 7,341,589 B2 | 3/2008 | Weaver et al. | |
| 7,354,441 B2 | 4/2008 | Frigg | |
| 7,604,657 B2 | 10/2009 | Orbay et al. | |
| 7,632,277 B2 | 12/2009 | Woll et al. | |
| 7,635,381 B2 | 12/2009 | Orbay | |
| 7,637,928 B2 * | 12/2009 | Fernandez ......... | A61B 17/8057 |
| | | | 606/289 |
| 7,655,029 B2 | 2/2010 | Niederberger et al. | |
| 7,695,472 B2 | 4/2010 | Young | |
| 7,722,653 B2 | 5/2010 | Young et al. | |
| 7,740,648 B2 | 6/2010 | Young et al. | |
| 7,776,076 B2 | 8/2010 | Grady, Jr. et al. | |
| 7,857,838 B2 | 12/2010 | Orbay | |
| 7,867,260 B2 | 1/2011 | Meyer et al. | |
| 7,867,261 B2 | 1/2011 | Sixto, Jr. et al. | |
| 7,875,062 B2 | 1/2011 | Lindemann et al. | |
| 7,905,910 B2 | 3/2011 | Gerlach et al. | |
| 7,909,858 B2 | 3/2011 | Gerlach et al. | |
| 7,951,178 B2 | 5/2011 | Jensen | |
| 7,951,179 B2 | 5/2011 | Matityahu | |
| 7,976,570 B2 | 7/2011 | Wagner et al. | |
| D643,121 S | 8/2011 | Millford et al. | |
| D646,785 S | 10/2011 | Milford | |
| 8,043,297 B2 | 10/2011 | Grady, Jr. et al. | |
| 8,057,520 B2 | 11/2011 | Ducharme et al. | |
| 8,062,296 B2 | 11/2011 | Orbay et al. | |
| 8,100,953 B2 | 1/2012 | White et al. | |
| 8,105,367 B2 | 1/2012 | Austin et al. | |
| 8,114,081 B2 | 2/2012 | Kohut et al. | |
| 8,118,846 B2 | 2/2012 | Leither et al. | |
| 8,162,950 B2 | 4/2012 | Digeser et al. | |
| 8,167,918 B2 | 5/2012 | Strnad et al. | |
| 8,177,820 B2 | 5/2012 | Anapliotis et al. | |
| 8,246,661 B2 | 8/2012 | Beutter et al. | |
| 8,252,032 B2 | 8/2012 | White et al. | |
| 8,257,403 B2 | 9/2012 | Den Hartog et al. | |
| 8,257,405 B2 | 9/2012 | Haidukewych et al. | |
| 8,257,406 B2 | 9/2012 | Kay et al. | |
| 8,262,707 B2 | 9/2012 | Huebner et al. | |
| 8,267,972 B1 | 9/2012 | Gehlert | |
| 8,317,842 B2 | 11/2012 | Graham et al. | |
| 8,323,321 B2 | 12/2012 | Gradl | |
| 8,337,535 B2 | 12/2012 | White et al. | |
| 8,343,155 B2 | 1/2013 | Fisher et al. | |
| 8,382,807 B2 | 2/2013 | Austin et al. | |
| 8,394,098 B2 | 3/2013 | Orbay et al. | |
| 8,394,130 B2 | 3/2013 | Orbay et al. | |
| 8,398,685 B2 | 3/2013 | McGarity et al. | |
| 8,403,966 B2 | 3/2013 | Ralph et al. | |
| 8,419,775 B2 | 4/2013 | Orbay et al. | |
| 8,435,272 B2 | 5/2013 | Dougherty et al. | |
| 8,439,918 B2 | 5/2013 | Gelfand | |
| 8,444,679 B2 | 5/2013 | Ralph et al. | |
| 8,491,593 B2 | 7/2013 | Prien et al. | |
| 8,506,608 B2 | 8/2013 | Cerynik et al. | |
| 8,512,385 B2 | 8/2013 | White et al. | |
| 8,518,090 B2 | 8/2013 | Huebner et al. | |
| 8,523,862 B2 | 9/2013 | Murashko, Jr. | |
| 8,523,919 B2 | 9/2013 | Huebner et al. | |
| 8,523,921 B2 | 9/2013 | Horan et al. | |
| 8,551,095 B2 | 10/2013 | Fritzinger et al. | |
| 8,568,462 B2 | 10/2013 | Sixto, Jr. et al. | |
| 8,574,268 B2 * | 11/2013 | Chan .................... | B23G 1/02 |
| | | | 606/280 |
| 8,597,334 B2 | 12/2013 | Mocanu | |
| 8,603,147 B2 | 12/2013 | Sixto, Jr. et al. | |
| 8,617,224 B2 | 12/2013 | Kozak et al. | |
| 8,632,574 B2 | 1/2014 | Kortenbach et al. | |
| 8,641,741 B2 | 2/2014 | Murashko, Jr. | |
| 8,641,744 B2 | 2/2014 | Weaver et al. | |
| 8,663,224 B2 | 3/2014 | Overes et al. | |
| 8,728,082 B2 | 5/2014 | Fritzinger et al. | |
| 8,728,126 B2 | 5/2014 | Steffen | |
| 8,740,905 B2 | 6/2014 | Price et al. | |
| 8,747,442 B2 | 6/2014 | Orbay et al. | |
| 8,764,751 B2 | 7/2014 | Orbay et al. | |
| 8,764,808 B2 | 7/2014 | Gonzalez-Hernandez | |
| 8,777,998 B2 | 7/2014 | Daniels et al. | |
| 8,790,376 B2 | 7/2014 | Fritzinger et al. | |
| 8,790,377 B2 | 7/2014 | Ralph et al. | |
| 8,808,333 B2 | 8/2014 | Kuster et al. | |
| 8,808,334 B2 | 8/2014 | Strnad et al. | |
| 8,834,532 B2 | 9/2014 | Velikov et al. | |
| 8,834,537 B2 | 9/2014 | Castaneda et al. | |
| 8,670,931 B2 | 10/2014 | Dahners et al. | |
| 8,852,246 B2 | 10/2014 | Hansson | |
| 8,852,249 B2 | 10/2014 | Ahrens et al. | |
| 8,864,802 B2 | 10/2014 | Schwager et al. | |
| 8,888,825 B2 | 11/2014 | Batsch et al. | |
| 8,906,076 B2 | 12/2014 | Mocanu et al. | |
| 8,911,482 B2 | 12/2014 | Lee et al. | |
| 8,926,675 B2 | 1/2015 | Leung et al. | |
| 8,940,026 B2 | 1/2015 | Hilse et al. | |
| 8,940,028 B2 | 1/2015 | Austin et al. | |
| 8,940,029 B2 | 1/2015 | Leung et al. | |
| 8,951,291 B2 | 2/2015 | Impellizzeri | |
| 8,968,368 B2 | 3/2015 | Tepic | |
| 9,011,457 B2 | 4/2015 | Grady, Jr. et al. | |

(56) References Cited

U.S. PATENT DOCUMENTS

| | | |
|---|---|---|
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,566,097 B2 | 2/2017 | Fierlbeck et al. |
| 9,636,157 B2 | 5/2017 | Medoff |
| 9,649,141 B2 | 5/2017 | Raven, III et al. |
| 9,668,794 B2 | 6/2017 | Kuster et al. |
| 2002/0045901 A1 | 4/2002 | Wagner et al. |
| 2004/0097937 A1 | 5/2004 | Pike et al. |
| 2005/0010226 A1* | 1/2005 | Grady, Jr. ............... A61B 17/74 606/281 |
| 2005/0107796 A1 | 5/2005 | Gerlach et al. |
| 2005/0131413 A1 | 6/2005 | O'Driscoll et al. |
| 2005/0165400 A1* | 7/2005 | Fernandez ......... A61B 17/8047 606/281 |
| 2005/0187551 A1 | 8/2005 | Orbay et al. |
| 2005/0261688 A1* | 11/2005 | Grady, Jr. .......... A61B 17/8057 606/286 |
| 2006/0009771 A1* | 1/2006 | Orbay ................ A61B 17/8057 606/291 |
| 2006/0149265 A1 | 7/2006 | James et al. |
| 2006/0241607 A1 | 10/2006 | Myerson et al. |
| 2007/0123873 A1* | 5/2007 | Czartoski ............... A61B 17/72 606/62 |
| 2007/0219636 A1* | 9/2007 | Thakkar ............. A61B 17/1721 623/18.11 |
| 2007/0270849 A1 | 11/2007 | Orbay et al. |
| 2008/0021477 A1 | 1/2008 | Strnad et al. |
| 2008/0140130 A1* | 6/2008 | Chan ................. A61B 17/1728 606/280 |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0211112 A1* | 8/2010 | Kuster ................. A61B 17/746 606/290 |
| 2010/0274247 A1 | 10/2010 | Grady, Jr. et al. |
| 2010/0312286 A1* | 12/2010 | Dell'Oca ........... A61B 17/8057 606/291 |
| 2011/0106086 A1 | 5/2011 | Laird |
| 2011/0190769 A1 | 8/2011 | Haininger |
| 2011/0218580 A1 | 9/2011 | Schwager et al. |
| 2011/0224736 A1 | 9/2011 | Humphrey |
| 2011/0301655 A1* | 12/2011 | Price ................. A61B 17/1728 606/86 R |
| 2012/0059424 A1 | 3/2012 | Epperly et al. |
| 2012/0191104 A1 | 7/2012 | Jost et al. |
| 2012/0209270 A1* | 8/2012 | Segina ............... A61B 17/8061 606/67 |
| 2012/0323284 A1 | 12/2012 | Baker et al. |
| 2013/0018426 A1 | 1/2013 | Tsai et al. |
| 2013/0060291 A1 | 3/2013 | Petersheim |
| 2013/0096630 A1* | 4/2013 | Lee .................... A61B 17/8057 606/286 |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0261622 A1* | 10/2013 | Bonjour ............. A61B 17/7233 606/64 |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer |
| 2014/0330320 A1 | 11/2014 | Wolter |
| 2014/0378973 A1* | 12/2014 | Mueckter ............... A61B 17/72 606/64 |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1* | 3/2015 | Marotta ............. A61B 17/8014 606/281 |
| 2015/0105629 A1 | 4/2015 | Laird |
| 2015/0105779 A1* | 4/2015 | Smith ................ A61B 17/1725 606/71 |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0262814 A1 | 9/2016 | Wainscott |
| 2016/0278828 A1 | 9/2016 | Ragghianti |
| 2016/0310183 A1 | 10/2016 | Shaw et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2016/0374738 A1 | 12/2016 | Smith et al. |
| 2017/0035478 A1 | 2/2017 | Andermahr et al. |

(56) References Cited

U.S. PATENT DOCUMENTS

| | | | |
|---|---|---|---|
| 2017/0042592 A1 | 2/2017 | Kim | |
| 2017/0042596 A9 | 2/2017 | Mighell et al. | |
| 2017/0049493 A1 | 2/2017 | Gauneau et al. | |
| 2017/0065312 A1 | 3/2017 | Lauf et al. | |
| 2017/0215931 A1 | 8/2017 | Cremer et al. | |

FOREIGN PATENT DOCUMENTS

| | | | |
|---|---|---|---|
| CN | 202821574 U | 3/2013 | |
| CN | 202821575 U | 3/2013 | |
| CN | 203506858 U | 4/2014 | |
| CN | 203815563 U | 9/2014 | |
| CN | 105982727 A | 10/2016 | |
| FR | 2846870 A1 | 5/2004 | |
| FR | 2928259 A1 | 9/2009 | |
| JP | 2003210478 A | 7/2003 | |
| TW | 201316942 A | 5/2013 | |
| WO | 2009042783 A2 | 4/2009 | |
| WO | 2014110421 A1 | 7/2014 | |
| WO | 2014134669 A1 | 9/2014 | |
| WO | 2016079504 A1 | 5/2016 | |

\* cited by examiner

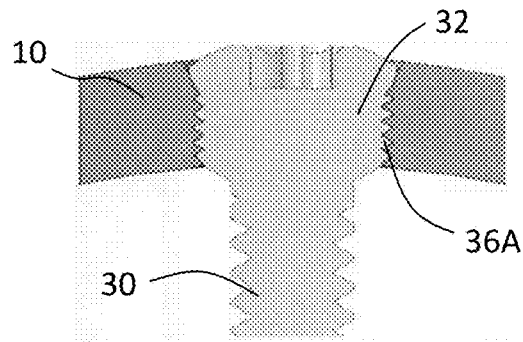
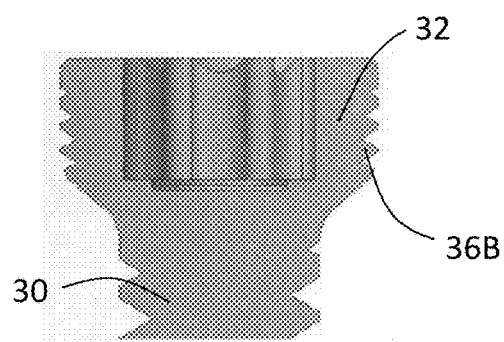
FIG. 14A  FIG. 14B
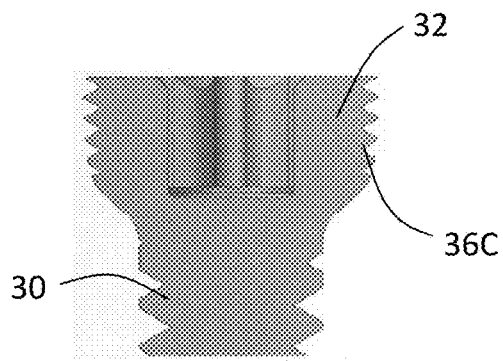
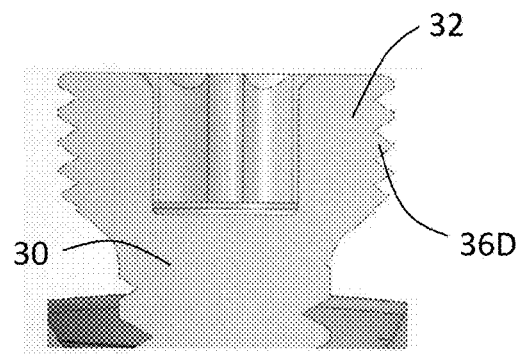
FIG. 14C  FIG. 14D
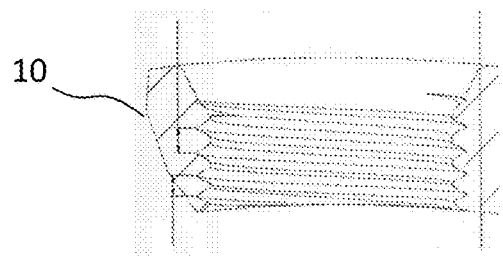
FIG. 14E

PROXIMAL HUMERAL STABILIZATION SYSTEM

CROSS REFERENCE TO RELATED APPLICATION

This application claims priority to U.S. provisional application No. 62/210,680, filed Aug. 27, 2015, which is hereby incorporated by reference in its entirety for all purposes.

FIELD

The present disclosure relates to surgical devices and stabilization systems, for example, for trauma applications, and more particularly, for stabilization of proximal humeral fractures.

BACKGROUND

Bone fractures are often repaired by internal fixation of the bone, such as diaphyseal bone, using one or more plates. The plate is held against the fractured bone with screws, for example, which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. There may be a desire to use locking screws, non-locking screws, or a combination of both that are able to dynamically compress the bone. Of course, the designs of the plates, types of screws, and locking and/or non-locking capabilities may vary based on the location and type of fracture.

The three long bones of the upper extremity are the humerus, radius, and ulna. In the case of proximal humerus fracture fixation, plating of the lateral bone surface may be desirable. In some cases, plating alone may lead to humeral head collapse during healing, and the addition of an allograft fibular strut inside of the intramedullary canal and inserted through the fracture site may prevent head collapse. There remains a need, however, for improved plating systems and/or intramedullary systems that provide appropriate stabilization to the humerus.

SUMMARY

To meet this and other needs, devices, systems, and methods of bone stabilization are provided, for example, for humerus stabilization. The proximal humerus stabilization systems may include one or more plates and one or more fasteners. The proximal humerus stabilization systems may also include an intramedullary nail and one or more fasteners extending therethrough. The plate and nail may each be used alone or may be used in combination together to stabilize a long bone, such as a humerus. Although generally described with reference to the humerus, it will be appreciated that the stabilization systems described herein may be used or adapted to be used for the fixation of other long bones as well, such as the femur, tibia, etc.

According to one embodiment, a stabilization system includes a bone plate, an intramedullary nail, and a plurality of fasteners. The bone plate comprises an elongated portion extending along a longitudinal axis and an enlarged head portion extending from the elongated portion, the bone plate comprising a plurality of through holes. The intramedullary nail comprises an upper portion and a lower portion extending from the upper portion, the upper portion and the lower portion including a plurality of holes. The intramedullary nail may be configured such that the lower portion of the intramedullary nail is received in an intramedullary canal and the upper portion is received in the head of the humerus. The fasteners are configured to extend through one or more of the plurality of through holes in the bone plate and one or more of the plurality of holes in the intramedullary nail and into the bone.

The fasteners may include locking fasteners (e.g., configured to lock to the plate and/or the intramedullary nail), non-locking fasteners (e.g., configured to provide dynamic compression of the bone), polyaxial fasteners (e.g., configured to be inserted at a plurality of angles or trajectories), fixed angle fasteners (e.g., configured to be inserted at a fixed angle or trajectory), or any other suitable fasteners known in the art. The plurality of through holes may comprise first and second polyaxial openings, and the plurality of fasteners may comprise polyaxial calcar screws configured to be received in the first and second polyaxial openings, and configured to be aimed at a calcar region of a proximal humerus. The plurality of through holes may comprise a plurality of fixed angle openings positioned on the enlarged head portion of the plate, and the plurality of fasteners may comprise fixed angle, locking screws configured to be received in the fixed angle openings and the upper portion of the intramedullary nail and configured to be aimed at a humeral head. The plurality of through holes may comprise a plurality of elongated slots positioned on the elongated portion of the plate, and the plurality of fasteners may comprise at least one polyaxial screw configured to be received in at least one of the plurality of elongated slots and within one of the plurality of holes in the lower portion of the intramedullary nail to permit dynamic compression of the bone. In some instances, the locking fasteners may include fasteners having self-forming threads on a head portion of the fasteners, which are configured to lock to at least one of the plurality of through holes on the plate.

According to another embodiment, a stabilization system configured to stabilize a humerus includes a bone plate, a plurality of polyaxial calcar fasteners, a plurality of fixed angle, locking fasteners, and at least one polyaxial, non-locking fastener. The bone plate includes an elongated portion extending along a longitudinal axis and an enlarged head portion extending from the elongated portion. The bone plate comprises first and second polyaxial openings, a plurality of fixed angle openings positioned on the enlarged head portion of the plate, and a plurality of elongated slots positioned on the elongated portion of the plate. The plurality of polyaxial calcar fasteners may be configured to be received in the first and second polyaxial openings and configured to be aimed at a calcar region of the humerus. The plurality of fixed angle, locking fasteners may be configured to be received in the plurality of fixed angle openings, respectively, and configured to be aimed at a humeral head of the humerus. The polyaxial, non-locking fastener may be configured to be received in one of the plurality of elongated slots to permit dynamic compression of the bone and configured to be aimed at a shaft of the humerus.

According to another embodiment, a stabilization system includes an implant and a plurality of fasteners. The implant has an upper portion and a lower portion, the upper portion configured and dimensioned to be cylindrical and the lower portion extending from the upper portion, the upper portion and the lower portion including a plurality of holes. The lower portion may be positioned in an intramedullary canal and the upper portion may be positioned in a humeral head. The plurality of fasteners may be configured to be received by the plurality of holes of the upper and lower portions of the implant.

According to yet another embodiment, one or more methods of installing a stabilization system may include aligning a bone plate to a lateral surface of the humerus, inserting an intramedullary nail such that the nail is at least partially received in the head of the humerus and the intramedullary canal of the shaft, and inserting one or more fasteners through the bone plate, through the intramedullary nail, and into the bone to stabilize the humerus and repair the fracture. Before the fasteners are inserted, one or more pilot holes may be pre-drilled and the bone plate and/or intramedullary nail may comprise one or more drill guides to aid in aligning the appropriate trajectories of the respective bone fasteners.

Also provided are kits for the stabilization systems including bone plates of varying sizes and orientations, intramedullary nails of varying sizes and orientations, fasteners including locking fasteners, non-locking, compression fasteners, polyaxial fasteners, fixed angle fasteners, or any other suitable fasteners, drill guides, k-wires, sutures, and other components for installing the same.

BRIEF DESCRIPTION OF THE DRAWING

A more complete understanding of the present invention, and the attendant advantages and features thereof, will be more readily understood by reference to the following detailed description when considered in conjunction with the accompanying drawings wherein:

FIGS. 14A-14E shows alternative locking screw and openings in plates according to yet another embodiment;

DETAILED DESCRIPTION

Figure 1A:
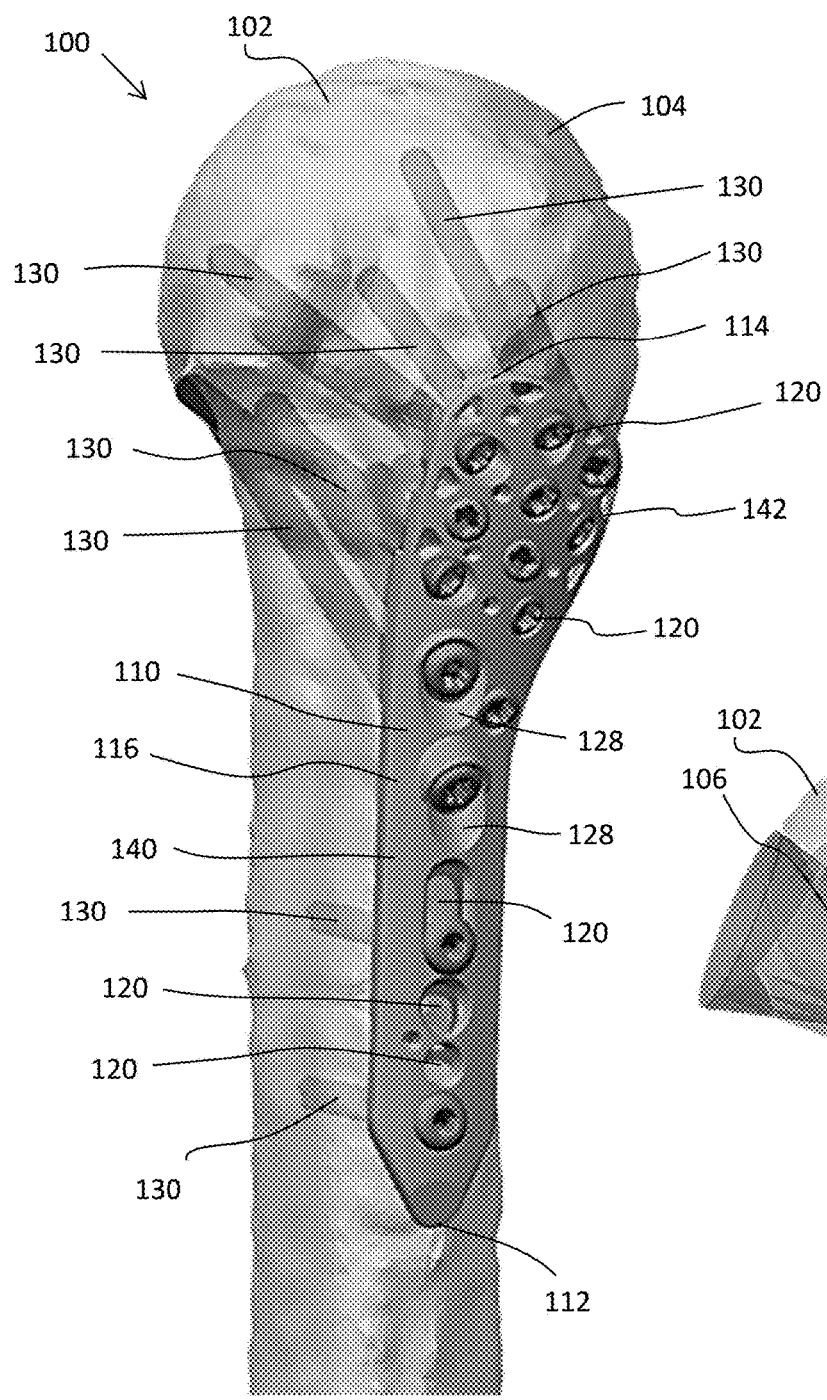
FIGS. 1A-1G depict a stabilization system according to one embodiment including a proximal humerus plate and a plurality of bone fasteners.

Embodiments of the disclosure are generally directed to devices, systems, and methods for bone stabilization, especially proximal humeral stabilization. Specifically, embodiments are directed to proximal humerus stabilization systems including a bone plate configured to sit on a lateral surface of the proximal humerus and supporting the fractured head of the humerus. Other embodiments are directed toward drill guides configured to guide predrilling of pilot holes for insertion into the bone plate. Further embodiments are direction alternative proximal humerus stabilization systems including a bone plate used in conjunction with an intramedullary nail. The fasteners may be configured to secure both the bone plate and the intramedullary nail. Still other embodiments are directed to different types of holes and fasteners configured to provide locking and/or compression to the bone.

The bone plate and/or intramedullary nail may be comprised of titanium, stainless steel, cobalt chrome, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates, intramedullary nails, and bone fasteners are made, it should be understood that the bone plates, intramedullary nails, and fasteners comprised of any appropriate material are contemplated.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Proximal Humeral Plate System

Referring now to the drawing, FIGS. 1A-1G depict an embodiment of a proximal humerus stabilization system 100 including a bone plate 110 configured to sit on a lateral surface of the proximal humerus 102 and supporting the fractured head 104 of the humerus 102 and one or more bone fasteners 130 configured to be received in the bone plate 110 and secured to the humerus 102. The humerus 102 is a long bone in the arm or forelimb that runs from the shoulder to the elbow. Although generally described with reference to the humerus 102, it will be appreciated that the stabilization systems described herein may be used or adapted to be used for the fixation of other long bones as well, such as the femur, radius, tibia, etc.

The bone plate 110 extends from a first end 112 configured to be positioned proximate to a distal portion of femur 102 to a second end 114 configured to be positioned proximate to the head 104 of the femur 102. The plate 110 includes a top surface 116 and an opposite, bottom surface 118 configured to contact adjacent bone. The top and bottom surfaces 116, 118 are connected by opposite side surfaces extending from the first to second ends 112, 114 of the plate 110. With emphasis on FIGS. 1F-1G, the bottom surface 118 of the plate 110 includes an anatomic contour configured to follow the best approximation of average proximal humerus anatomy, wrapping posteriorly towards the proximal portion of the plate 110, thereby buttressing the greater tuberosity. The plate 110 is designed to sit low avoiding acromial impingement. The plate 110 further has a low profile proximal portion. The plate 110 tapers towards the proximal portion of the plate 110 with a very thin cross section to avoid impingement. The plate 110 gets thicker distally to support load across fracture site. In longer plates 110 (e.g., 135 mm and longer), the plate 110 may have a thicker cross section distally to allow surgeons to adequately stabilize multiple fractures or a long spiral proximal humerus fracture that translates down the shaft of the humerus 102. This consideration may be especially important when fixing a fracture using the bridging technique (e.g., bridging a fracture) when plate stress may be higher.

The bone plate 110 includes an elongated portion 140 extending along a longitudinal axis L having a length greater than its width. The elongated portion 140 is configured to contact the shaft of the femur 102. The elongated portion 140 may terminate at the first end 112 with a taper such that it has a width and/or thickness less than the remainder of the elongated portion 140. The bone plate 110 also includes an enlarged head portion 142 extending from the elongated portion 140. The enlarged head portion 142 or a portion thereof is configured to contact the head 104 of the femur 102. The enlarged head portion 142 has a width greater than the width of the elongated portion 140. The enlarged head portion 142 extends along an axis A at an angle relative to the longitudinal axis L of the elongated portion 140. The angle of the head portion 142 relative to the elongated portion 140 may range from about 10-60°, about 20-50°, about 30-40°, about 40-50°, or another appropriate angle. As best seen in FIG. 1D, the bone plates 110 may be available in a variety of lengths based on the anatomy of the patient. The plates 110 are configured to sit on the lateral surface of the proximal humerus 102 and supporting the head 104 of the humerus 102. The plates 110 are configured in both left and right designs, in a mirrored configuration, in order to address the anatomy of both the left and right arms of the patient.

Figure 1B:
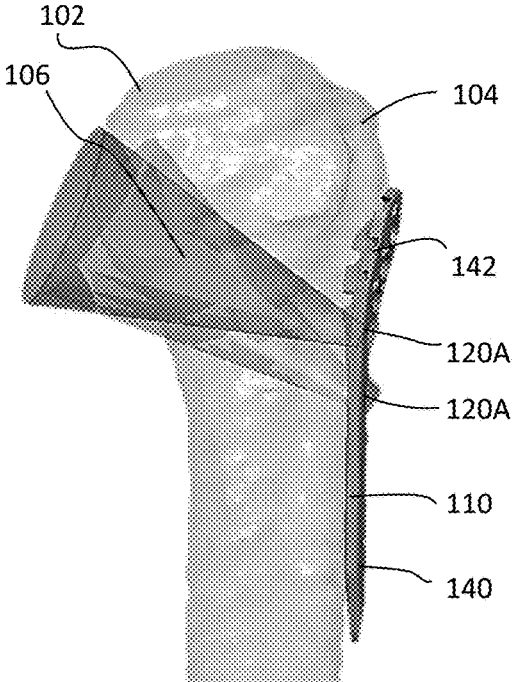
Figure 1C:
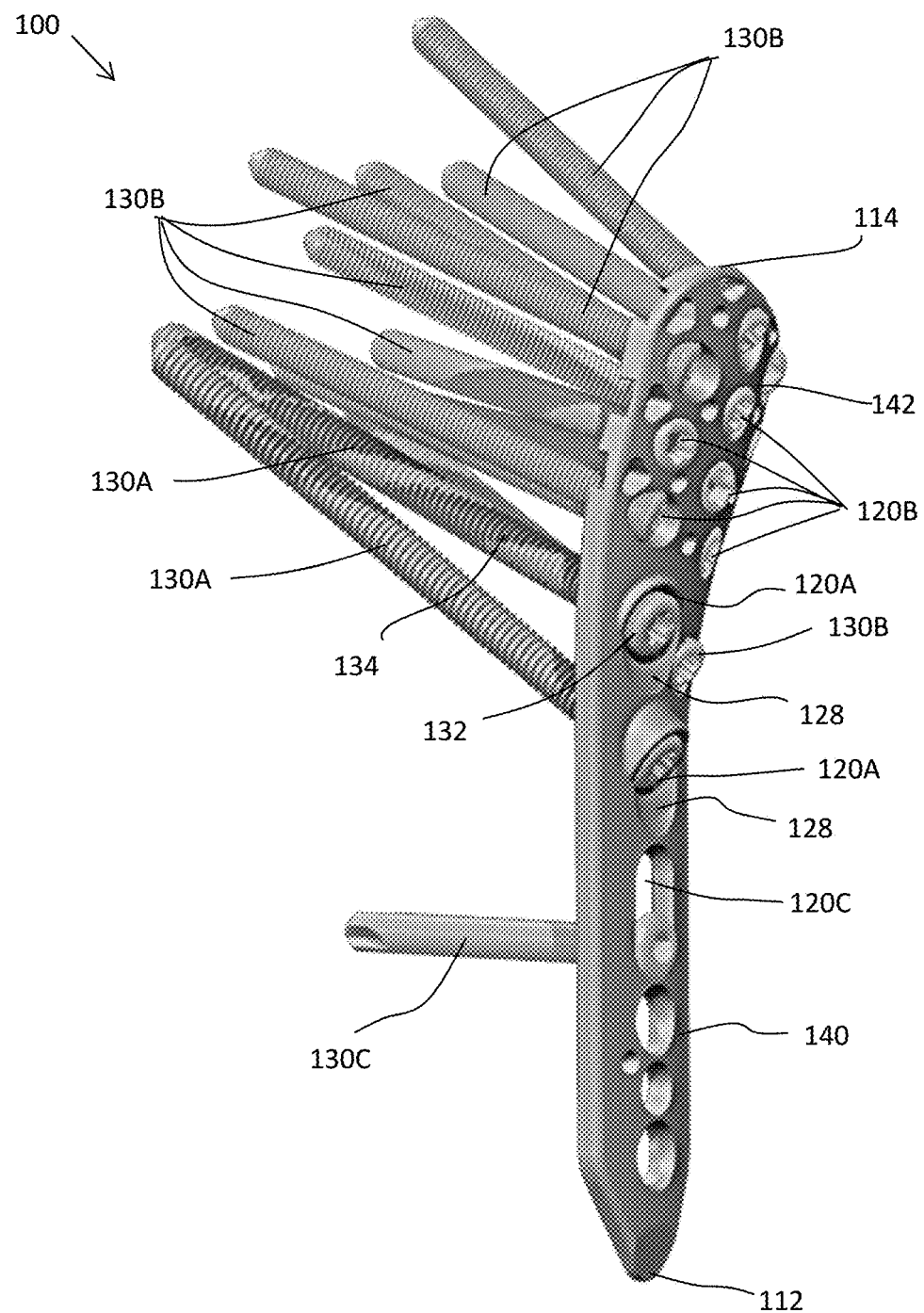
Figure 1D:
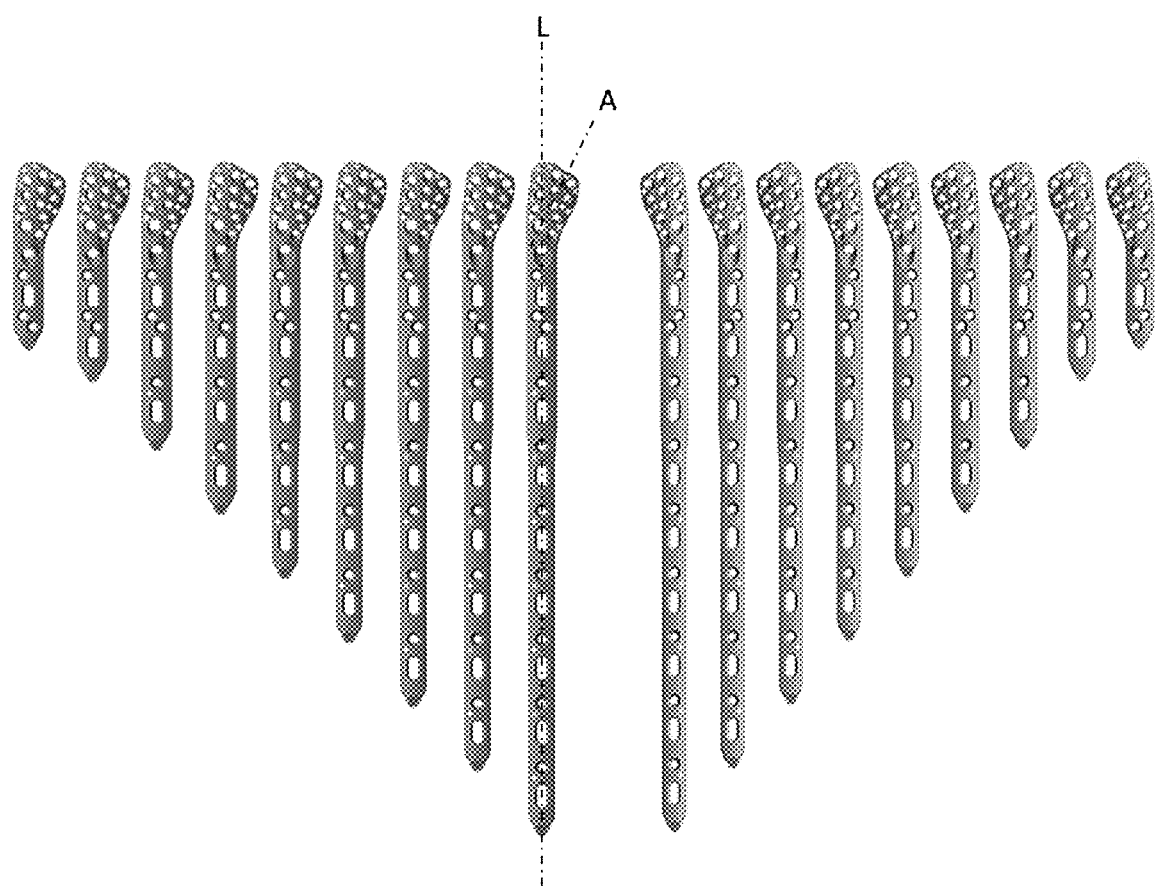
Figure 1E:
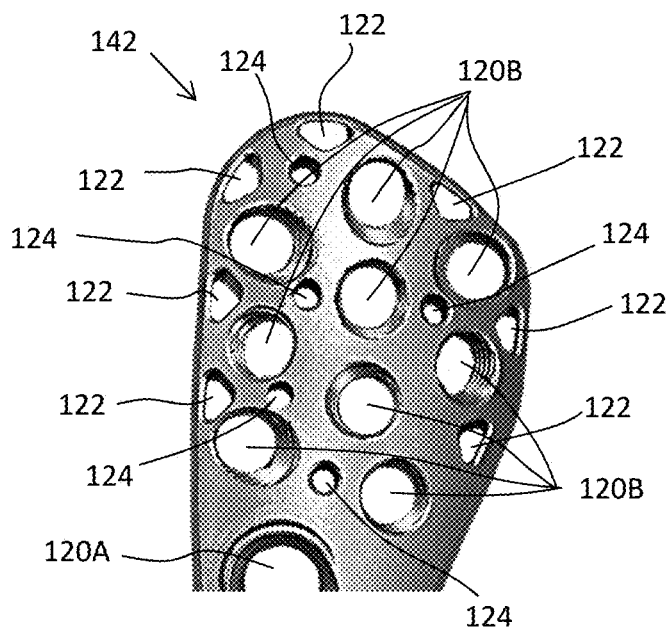
Figure 1F:
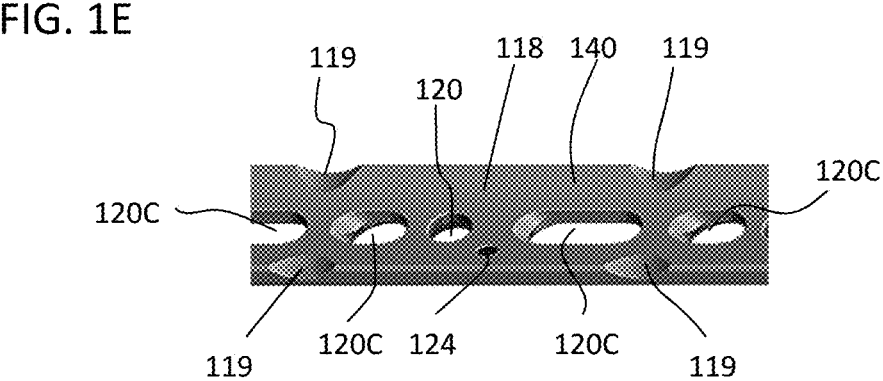
Figure 1G:
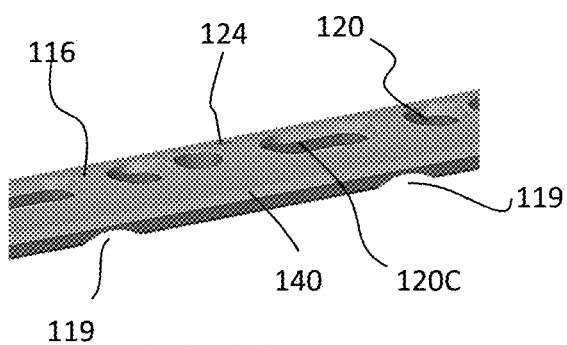
Figure 2A:
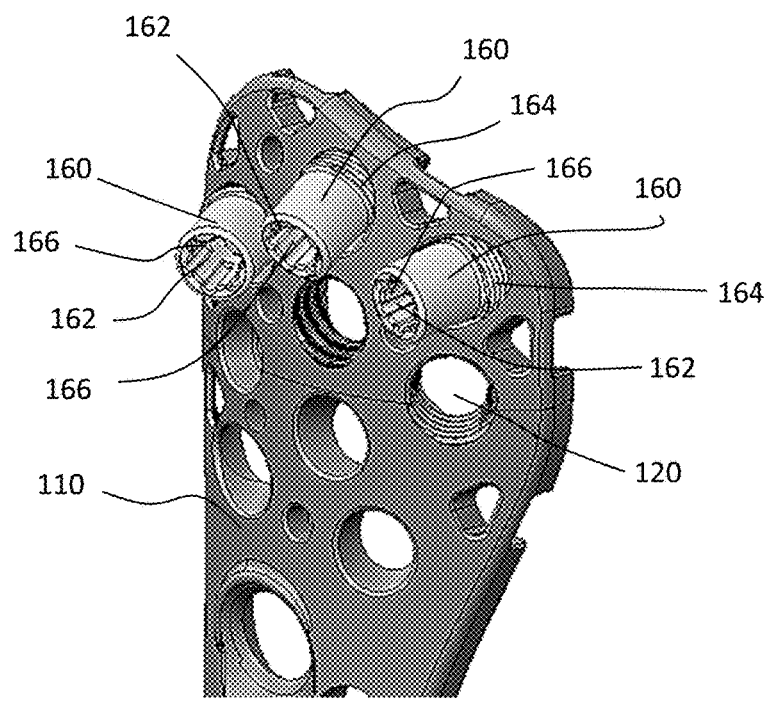
FIGS. 2A-2F depict pre-loaded drill guides suitable for use with the stabilization system described with respect to FIGS. 1A-1G.
Figure 2B:
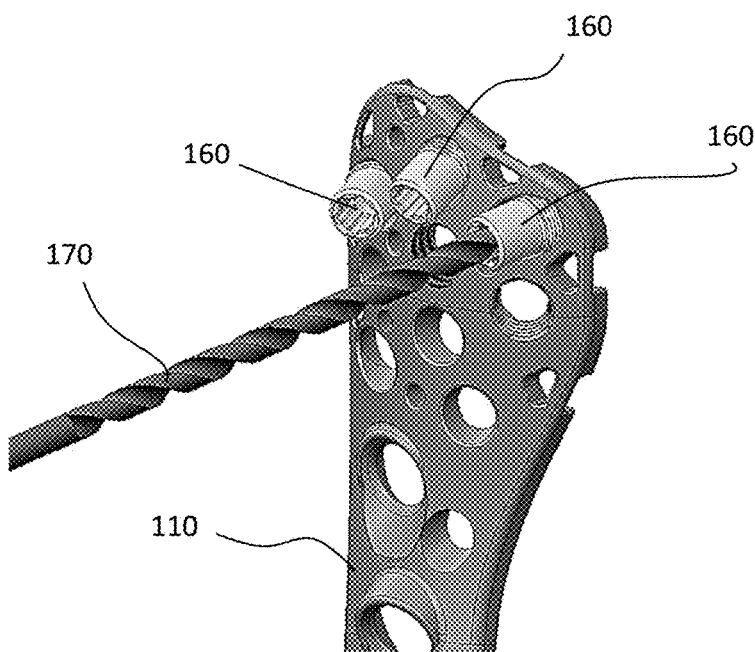
Figure 2C:
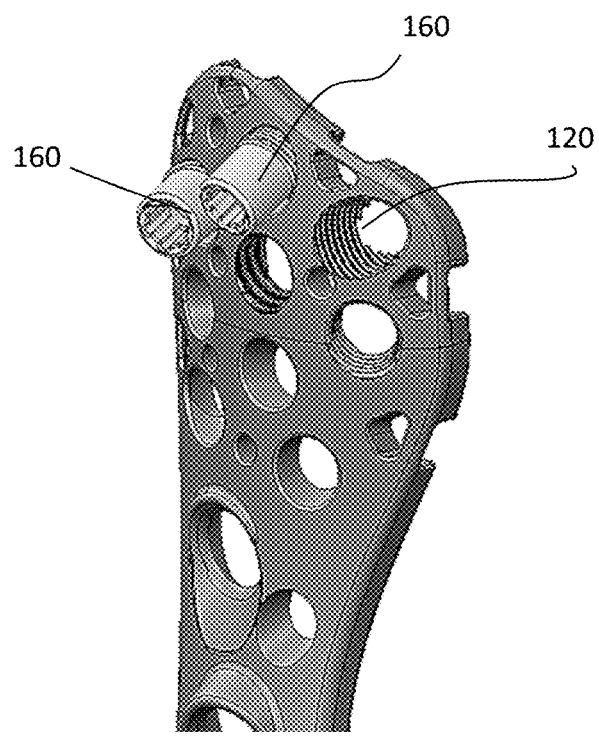
Figure 2D:
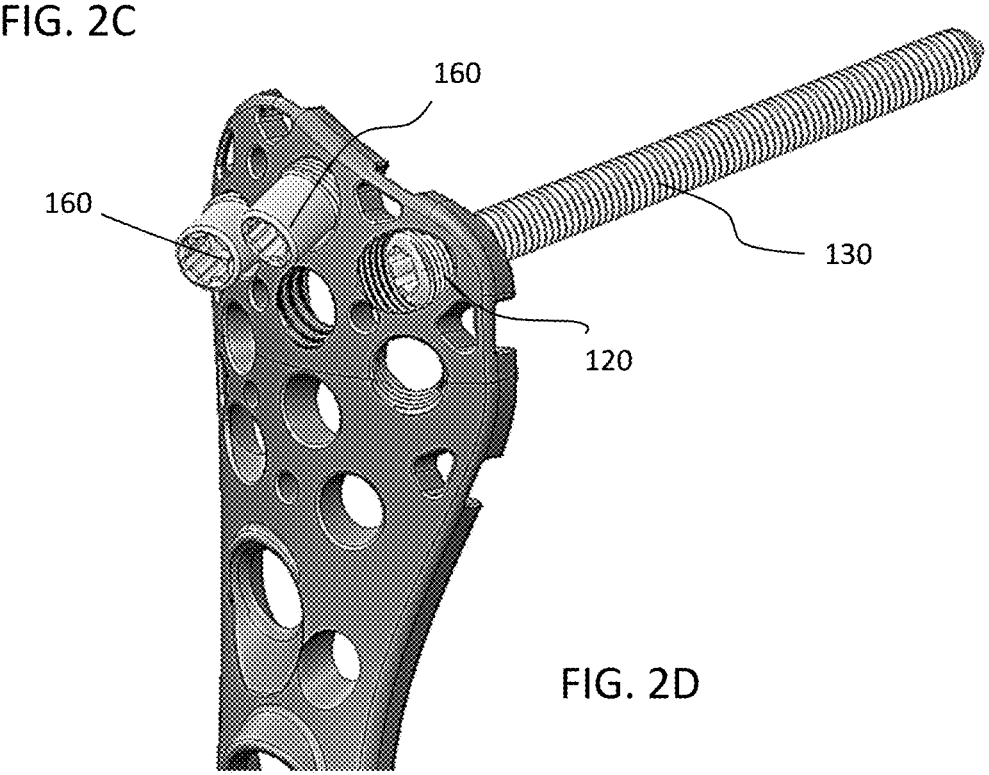
Figure 2E:
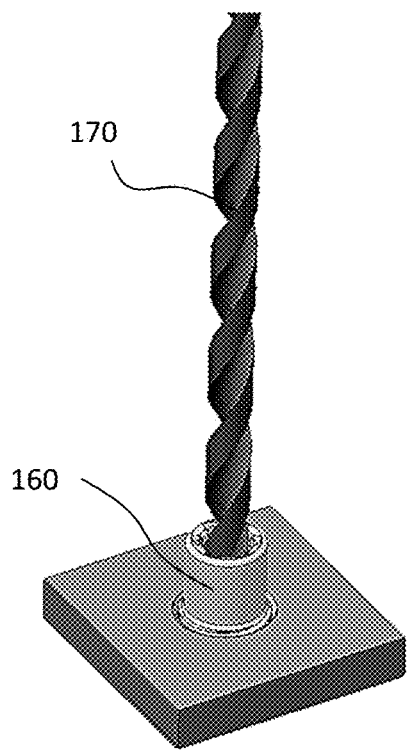
Figure 2F:
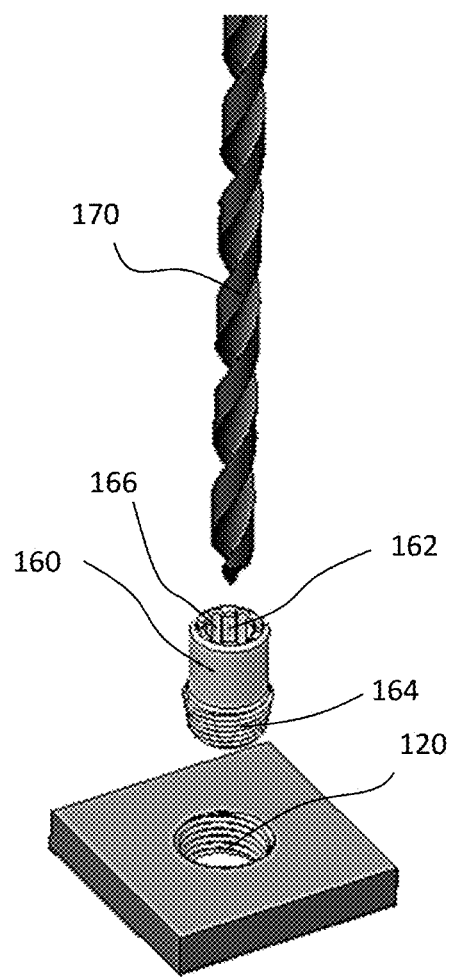

As best seen in FIGS. 1F and 1G, the bottom surface 118 of the plate 110 may include a plurality of scallop cuts 119 located along the elongated portion 140 between the fastener openings 120. The scallop cuts 119 may be in the form of partially cylindrical valleys cut around a periphery of the bottom surface 118 of the plate 110. This shields stress from the fastener openings 120 during bending, discouraging hole warping effects while recontouring the plate 110. This also reduces contact between the plate 110 and the bone surface, thereby helping to preserve blood supply to the bone and prevent osteonecrosis. In addition to the scallop cuts 119, a plurality of dimples may be positioned along the bottom surface 118 of the plate 110 (e.g., along the entire bottom surface 118 or a portion thereof) to further reduce contact between the plate 110 and bone surface, further helping to preserve blood supply and prevent osteonecrosis.

The plate 110 includes one or more through openings 120 configured to receive one or more bone fasteners 130. The openings 120 extend through the body of the plate 110 from the top surface 116 to the bottom surface 118. The openings 120 may include cylindrical openings, conical openings, elongated openings, threaded openings, textured openings, non-threaded and/or non-textured openings, and the like. The openings 120 may allow for locking of the fastener 130 to the plate 110 or may allow for movement and dynamic compression of the bone. The plate 110 may comprise any suitable number of openings 120 in any suitable configuration. These openings 120 allow surgeons more flexibility for fastener placement, based on preference, anatomy, and fracture location. Surgeons may have differing opinions as to the number, location, and types of fasteners 130. Further, complexity of fracture location and shape makes having as many locations for fasteners 130 as possible necessary. This design offers surgeons a versatile method to achieve higher accuracy in placement of the fasteners 130.

The openings 120 may be configured to receive one or more bone fasteners 130. The fasteners 130 may include locking fasteners, non-locking fasteners, or any other fasteners known in the art. The fasteners 130 may comprise bone screws or the like. The fasteners 130 may also include other fasteners or anchors configured to be secured or engaged with bone, such as nails, spikes, staples, pegs, barbs, hooks, or the like. The fasteners 130 may include fixed and/or variable angle bone screws. The fastener 130 may include a head portion 132 and a shaft portion 134 configured to engage bone. For a locking fastener 130, the shaft portion 134 may be threaded such that the fastener 130 may be threaded into the bone. The head portion 132 may include a textured area, such as threads, around its outer surface sized and configured to engage with the opening 120, for example, and corresponding threads in the opening 120 in order to lock the fastener 130 to the plate 110. In the alternative, for a non-locking fastener 130, the head portion 132 may be substantially smooth to allow for dynamic compression of the bone.

As best seen in FIGS. 1B and 1C, the openings 120 include two holes 120A present in the midsection of the plate 110 that are nominally aimed toward the calcar region 106 of the proximal humerus 102, which may constitute the best quality bone in the region. The holes 120A may be polyaxial openings configured to accept fasteners 130A that can be aimed at the calcar region 106 for best bone purchase. The fasteners 130A may be aimed, for example, within a 40° cone at the calcar region 106. An upper portion of the hole 120A may be tapered 128 and a portion of the plate 110 around the hole 120A may be enlarged or increased in thickness to allow for the proper angle of the fasteners 130A to be achieved.

These fasteners 130A may be in the form of polaxial calcar bone screws. The calcar fasteners 130A may be generally larger (e.g., in length and/or diameter) than the other fasteners securing the plate 110 to the bone. The fasteners 130A are optionally cannulated to allow for precise placement with a k-wire (not shown) if desired by the surgeon. Another advantage of the polyaxial calcar fastener 130A is that the plate 110 can be placed in a wide range of locations in the proximal/distal direction, allowing the surgeons to avoid impingement, especially in small bones, and still achieve excellent purchase in the calcar 106 because of the polyaxiality of the fastener 130A. The calcar fasteners 130A may include polyaxial screws having self-forming threads that work by displacement of the plate material, which are described in more detail herein. The plate 110 may further include an opening 120 configured to receive a fixed angle calcar fastener 130B. The fixed angle calcar fastener 130B may be positioned in the mid-section of the plate 110 if the surgeon would like to use the fixed angle fastener 130B to line up the plate 110 relative to the bone.

Turning now to FIG. 1E, the openings 120 further include a plurality of holes 120B present in the head portion 142 of the plate 110. These holes 120B may be nominally aimed toward the head 104 of the humerus 102. The holes 120B may be fixed openings configured to accept fixed angle fasteners 130B that can be secured into the head 104 of humerus 102. The fasteners 130B may have predetermined trajectories based on the orientations of the openings 120B. An upper portion of the holes 120B may be tapered 128 to allow for the proper positioning of each of the fasteners 130B. Each of the fasteners 130B may be angled along a different trajectory than the other respective fasteners 130B. Some of the fasteners 130B may have a greater angulation than other respective fasteners 130B. As shown, the holes 120B receive nine fixed angle fasteners 130B in the humeral head 104 having predefined trajectories forming divergent and convergent patterns. The convergent patterns act as a buttress in supporting the low density bone in the center of the head 104. The divergent screws reach out to the anterior, posterior and superior portions of the humeral head 104. The screw holes 120B and screw heads 132 may have mating conical threads that lock the screw 130B in both angular and axial alignment to prevent collapse and backout.

With emphasis on FIGS. 1C and 1F, the openings also include one or more holes 120C present along the elongated portion 140 of the plate 110 and configured to accommodate a compression fastener 130C. The hole or holes 120C may be elongated along the longitudinal axis L of the elongated portion 140. The holes 120C may include ramped surfaces on the ends to permit dynamic compression plating. The elongated hole(s) 120C are situated in the distal portion of the plate 110. The elongated holes 120C may have varying lengths. As seen in FIG. 1D, additional compression holes 120C may be provided for the longer plate constructs. The holes 120C are configured to accommodate non-locking, compression screws 130C the heads of which have a spherical underside so the screw 130C may be placed at varying angles. The compression screw 130C can be inserted and preliminarily tightened to secure the plate 110 to the bone. As the screw 130C is inserted eccentrically in to the hole 120C, the screw 130C slides down the slot 120C, displacing the plate 110 and the bone as well. The compression screw 130C may have a shorter length and/or a smaller diameter than the proximal head screws 130B. If the plate 110 needs to be adjusted later, the screw 130C can be loosened and the plate 110 can be shifted in the proximal and/or distal directions. This slot 120C also accommodates reduction of the humeral shaft by inserting a very long compression screw 130C and pulling the bone to the plate 110.

As best seen in FIG. 1E, the head portion 142 of the plate 110 may also comprise a plurality of openings 122 configured as suture holes to receive sutures to secure the plate 110 to surrounding tissue. The suture openings 122 may include a plurality of generally triangular-shaped holes situated around the perimeter of the proximal section of the plate 110. The suture openings 122 may be amply sized to fit commonly used sutures and needles. The openings 122 may have undercuts (e.g., recesses on the bottom surface 118) to fit the suture even when the plate 110 is fully compressed to the bone. The openings 122 may also have generous rounds, as to not cut through suture wire while in use.

The plate 110 may further comprise a plurality of openings 124 configured to receive one or more k-wires (not shown). The k-wire holes 124 may comprise small diameter holes (e.g., having a diameter significantly smaller than the fastener openings 120). The k-wire holes 124 may be located in both proximal and distal sections of the plate 110 to allow preliminary placement of the plate 110 against the bone and/or to aid in reduction of the fracture. Distal k-wire holes 124 follow the anterior side of the plate 110 to make k-wire placement easier in the anterolateral approach.

The bone plate 110 may be attached to a proximal humerus to fixate one or more bone fractures or fragments and thereby promote healing of the bone. The plate 110 further restores the anatomic alignment of the proximal humerus 102. The plate 110 may be positioned against the lateral surface of the humerus 102. One or more k-wires may be supplied through the k-wire holes 124 to assist with preliminary placement of the plate 110. One or more sutures may be tied through the suture holes 122 to secure the plate 110 to the tissue before or after the fasteners 130 are inserted. Pilot holes may be drilled through the fastener openings 120 to prepare to receive the respective fasteners 130. The fasteners 130A, 130B, 130C may be positioned through the respective openings 120A, 120B, 120C and into the humerus 102. The fasteners 130 may be affixed to the bone in any suitable order, number, and orientation depending on the anatomy of the bone and the fracture.

Drill Guides

In some embodiments, it may be desirable to drill pilot holes before insertion of the fasteners 130. FIGS. 2A-2F depict one embodiment of drill guides 160 that may be suitable for use with the bone plate 110. Drill guides 160 allow a drill 170 to create a hole at the trajectory that the fastener 130 is intended to be inserted, guaranteeing that the pilot hole will be aligned with how the fastener 130 is designed to be inserted into the plate 110. According to one embodiment, the plates 110 may have drill guides 160 pre-installed into the plate 110 by the manufacturer. The pre-installed drill guides 160 may save the surgeon time in switching between instruments to drill pilot holes in the operating room. In the alternative, the drill guides 160 may be attached to the plate 110 at any suitable time before or during the operation.

The bone plates 110 may be designed to accommodate locking fasteners 130 which anchor into bone and lock to the plate 110 creating a fixed construct. Depending on the opening 120 in the plate 110, the fasteners 130 may be intended to have one fixed, nominal trajectory in which they can be inserted into the plate 110 for proper locking to occur. A tapered external thread on the head portion 132 of the fastener 130 is configured to interface with an internal tapered thread in the opening 120 of the plate 110, thereby locking the fastener 130 to the plate 110.

Instead of traditional single drill guides, which require the guide to be positioned over each respective opening 120, each plate 110 may have drill guides 160 already inserted into therein at each respective locking hole 120. The surgeon would then be able to immediately drill the pilot hole, for example, with the drill 170, through the pre-installed drill guide 160 without having the extra step of loading a traditional drill guide for each fastener 130 to be inserted. After the fastener 130 is inserted, the screw guide 160 may be removed, for example, with a self-retaining hexalobular or hexagonal female recess 162 on the top of the drill guide 160.

The pilot holes may be drilled after the plates 110 are provisionally placed, and before insertion of bone fasteners 130 into the bone. Many locking holes 120 have trajectories that are not oriented normal to the top surface 116 of the plate 110, and therefore can be difficult to thread in without knowing the nominal trajectory. Accordingly, the screw guides 160 will further provide an easy way to achieve the desired trajectory, and the pilot hole(s) can define the trajectory that the fastener 130 will follow during insertion. In order for the construct to lock properly, the trajectory of the fastener 130 should be correct so that the complimentary tapered threads of the fastener 130 and the opening 120 are able to interface.

The pre-installed drill guide 160 may extend from a first end to a second end configured to be received in one of the openings 120 in the plate 110. To engage the plate 110, the second end of the drill guide 160 may include a plurality of external threads 164 configured to engage corresponding threads in the opening 120. The external thread 164 may extend along a portion of the length of the drill guide 160 (e.g., less than half or less than a third of the length) or along the entire length of the drill guide 160. The drill guide 160 may have a head similar to the head portion 132 of the locking bone fastener 130, for example, on the bottom, with a round section protruding from the top of the plate 110. The center of the guide 160 may include a hole or cannulated opening 166 extending through its entirety with a diameter slightly larger than the drill 170 to allow for a slip fit. The first end of the drill guide 160 may include the female recess 162, such as but not limited to hexalobe or hexagon, and being larger than the cannulated hole 166 for guide removal. The female recess 162 for removal may be self-retaining so that the drill guide 160 can be removed and stay in place on the driver for removal from body. In an alternative embodiment, the outside of the drill guide 160 is shaped as a male feature, such as a hexagon, for removal with the use of a socket-like driver or the like.

Figure 3:
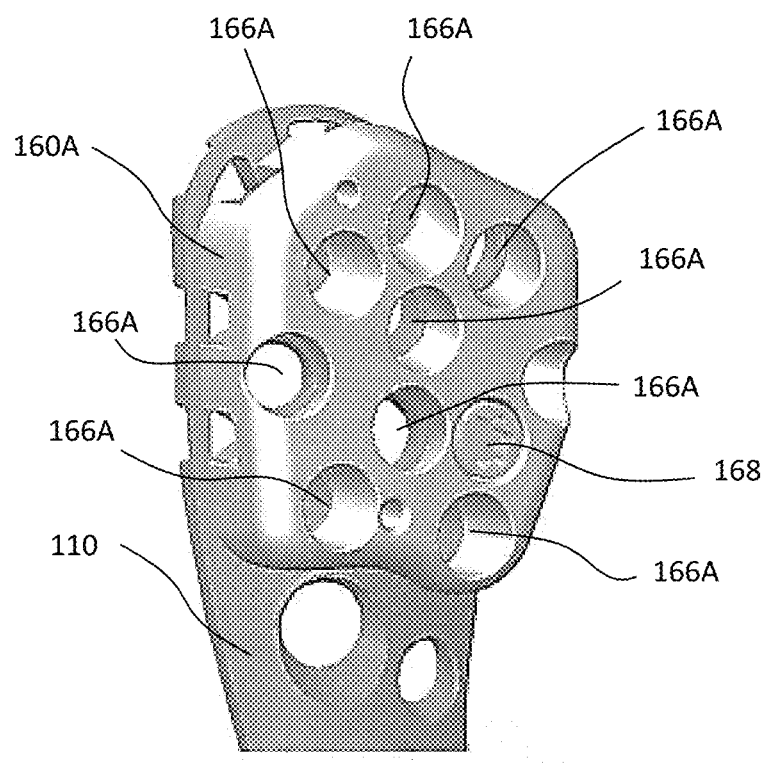
FIG. 3 depicts an alternative version of a drill guide according to another embodiment.

FIG. 3 depicts an alternative version of a drill guide 160A that can be attached to the proximal portion 142 of the plate 110. The drill guide 160A may include a plurality of cannulated openings 166A which correspond to each of the respective fixed angle openings 120 in the plate 110. The drill guide 160A openings 166A may be configured in order to drill the pilot holes at the appropriate trajectories for each opening 120, and subsequently receive the respective fasteners 130 at the correct trajectories. The drill guide 160A may also include a plurality of k-wire openings which match with the k-wire openings 124 in the plate 110. The drill guide 160A may be secured to the plate 110 with one or more fasteners 168. The fastener 168 may thread into the plate 110 or otherwise temporarily secure the drill guide 160A to the plate 110. The drill guide 160A may be pre-assembled to the plate 110 or may be attached at any other suitable time before or during the surgery. The fastener 168 may be secured, for example, in the operating room, via thumb or hexalobular fastener, to attach the drill guide 160A to the plate 110. After the pilot holes are drilled, the drill guide 160A may then be removed and the fasteners 130 positioned through the respective openings 120. The drill guide 160A may be relatively slim in thickness, for example, not protruding more than 10 mm above the plate 110, to allow for manipulation of the humerus 102 while not impinging on soft tissue.

Proximal Humeral Plate and Intramedullary Nail System

According to another embodiment exemplified in FIGS. 4A-4F, the proximal humerus stabilization system 200 may include a bone plate 210 configured to sit on a lateral surface of the proximal humerus 102 and supporting the fractured head 104 of the humerus 102, an intramedullary nail 250 configured to be positioned inside the intramedullary canal of the humerus 102, and one or more bone fasteners 230 configured to be received through the bone plate 110 and the intramedullary nail 250 and secured to the humerus 102.

The bone plate 210 may include similar features as the standalone bone plate 110 described above. As best seen in FIG. 4B, the bone plate 210 extends from first end 212 to second end 214 and includes top surface 216 and opposite, bottom surface 218 configured to contact adjacent bone. The bone plate 210 includes elongated portion 240 extending along longitudinal axis L having a length greater than its width and including enlarged head portion 242 extending from the elongated portion 240. The enlarged head portion 242 may extend along axis A at an angle relative to the longitudinal axis L of the elongated portion 240.

Similar to plate 110, plate 210 includes one or more through openings 220 configured to receive one or more bone fasteners 230. The openings 220 may include cylindrical openings, conical openings, elongated openings, threaded openings, textured openings, non-threaded and/or non-textured openings, and the like. The fasteners 230 may include locking fasteners, non-locking fasteners, or any other fasteners known in the art. The openings 220 may allow for locking of the fastener 230 to the plate 210 or may allow for movement and dynamic compression of the bone. The plate 210 may comprise any suitable number of openings 220 in any suitable configuration.

The fasteners 230 may include fixed and/or variable angle bone screws. The fastener 230 may include head portion 232 and shaft portion 234 configured to engage bone. The shaft portion 234 may be threaded such that the fastener 230 may be threaded into the bone. For a locking fastener 230, the head portion 232 may include a textured area, such as threads, around its outer surface sized and configured to engage with the opening 220, for example, and corresponding threads in the opening 220 in order to lock the fastener 230 to the plate 210. In the alternative, for a non-locking fastener 230, the head portion 232 may be substantially smooth to allow for dynamic compression of the bone.

As best seen in FIG. 4B, similar to plate 110, the plate 210 includes two holes 220A present in the midsection of the plate 210 that are nominally aimed toward the calcar region 106 of the proximal humerus 102. The holes 220A may be polyaxial openings configured to accept polyaxial calcar fasteners 230A that can be aimed at the calcar region 106 for best bone purchase. A portion of the hole 220A (e.g., around the perimeter on the top surface 216) may be tapered 228 to allow for the trajectory of the fasteners 230A to reach the calcar region 106. The plate 210 may further include an opening 220B configured to receive a fixed angle calcar fastener 230B. The plate 210 may further include a plurality of fixed angle holes 220B present in the head portion 242 of the plate 210, which are nominally aimed toward the head 104 of the humerus 102. The fixed angle fasteners fasteners 230B may have predetermined trajectories based on the orientations of the openings 220B. As shown, the holes 220B receive seven fixed angle fasteners 230B. The plate 210 may also include one or more elongated holes 220C present along the elongated portion 240 of the plate 210 and configured to accommodate a compression and/or locking fastener 230C. The head portion 242 of the plate 210 may also comprise a plurality of suture holes or openings 222 configured to receive sutures and secure the plate 210 to surrounding tissue, and a plurality of k-wire holes or openings 224 configured to receive one or more k-wires (not shown).

Figure 4A:
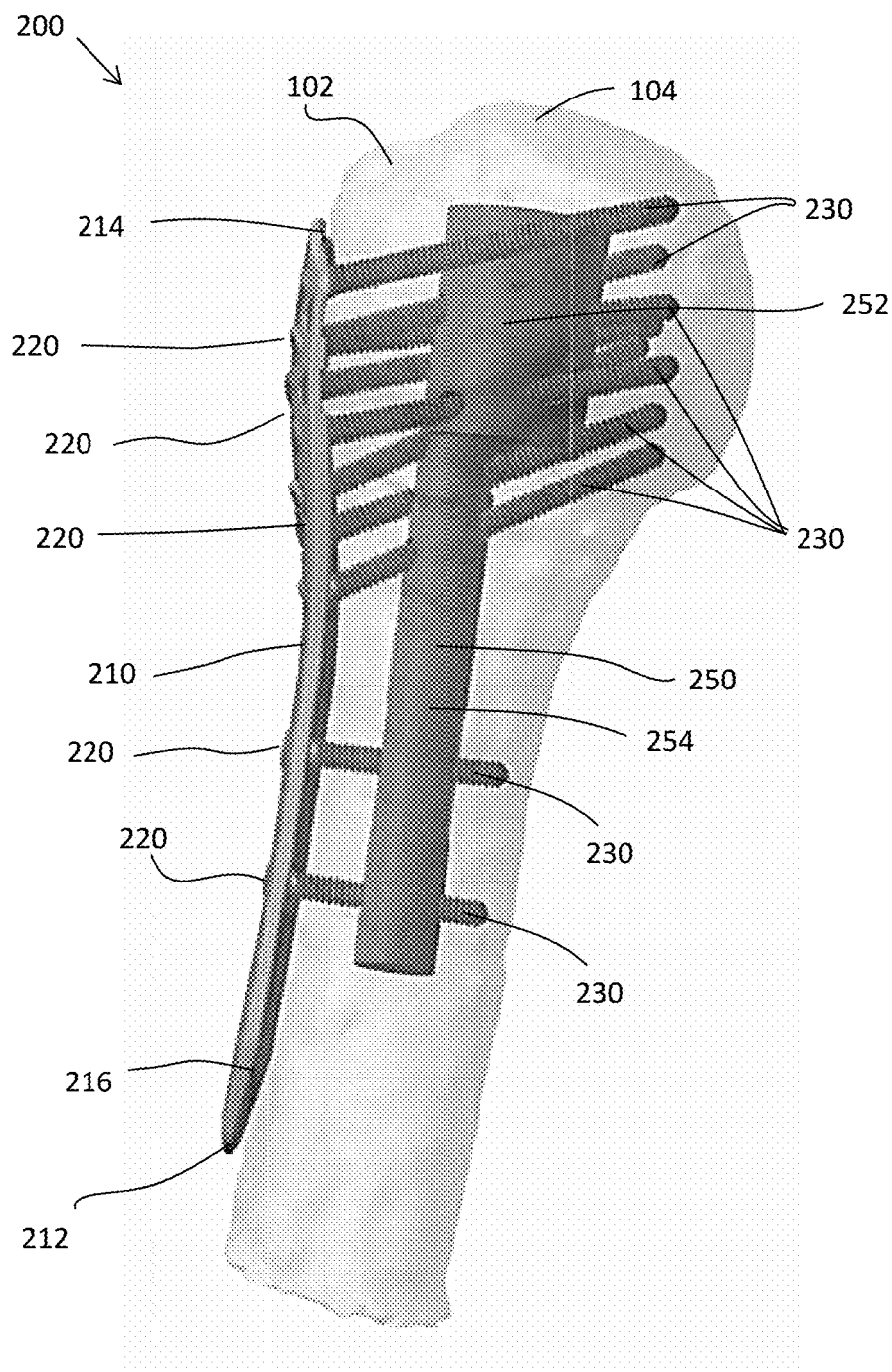
FIGS. 4A-4H show a stabilization system according to another embodiment including a proximal humerus plate and an intramedullary nail secured with a plurality of bone fasteners.
Figure 4B:
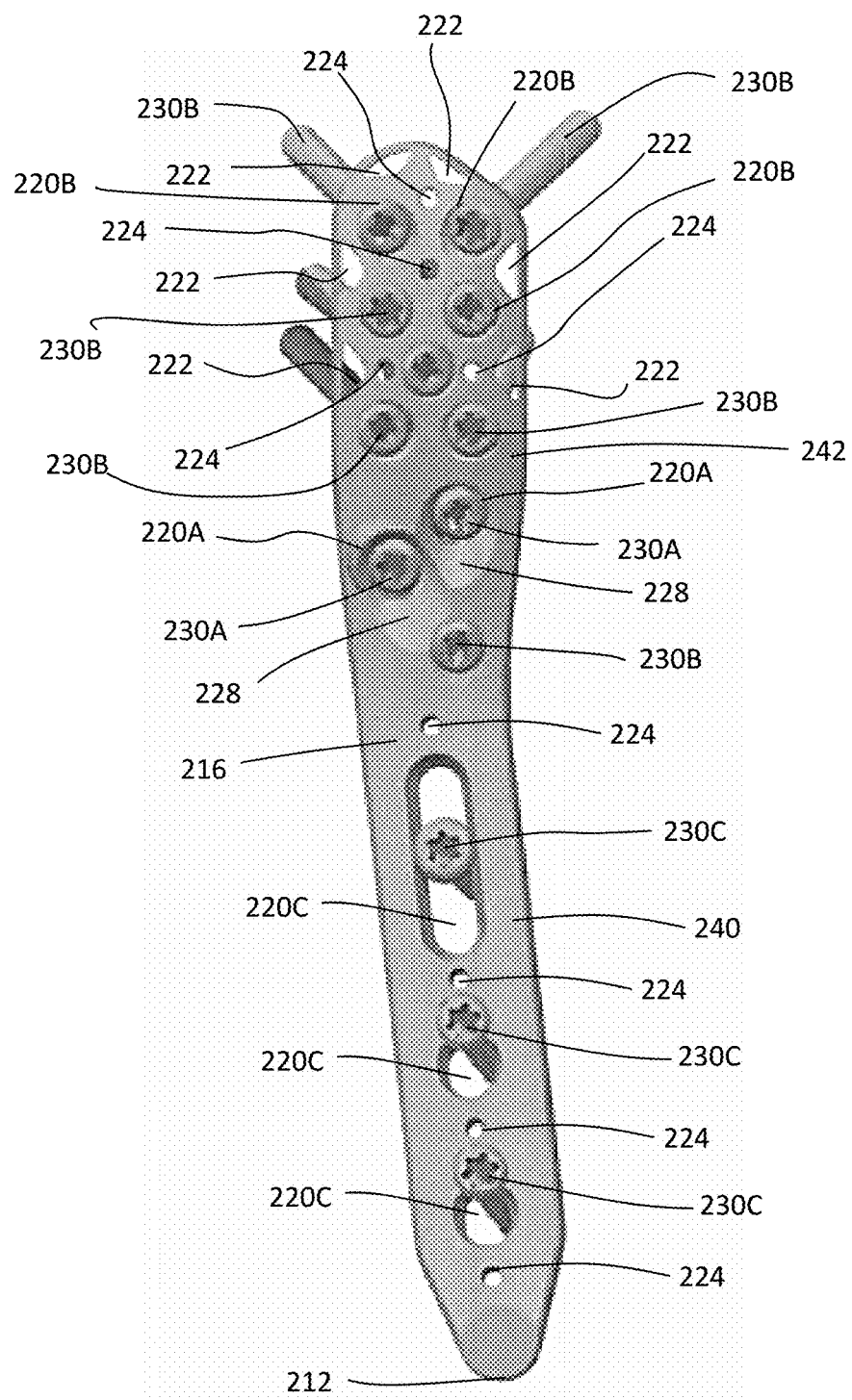
Figure 4C:
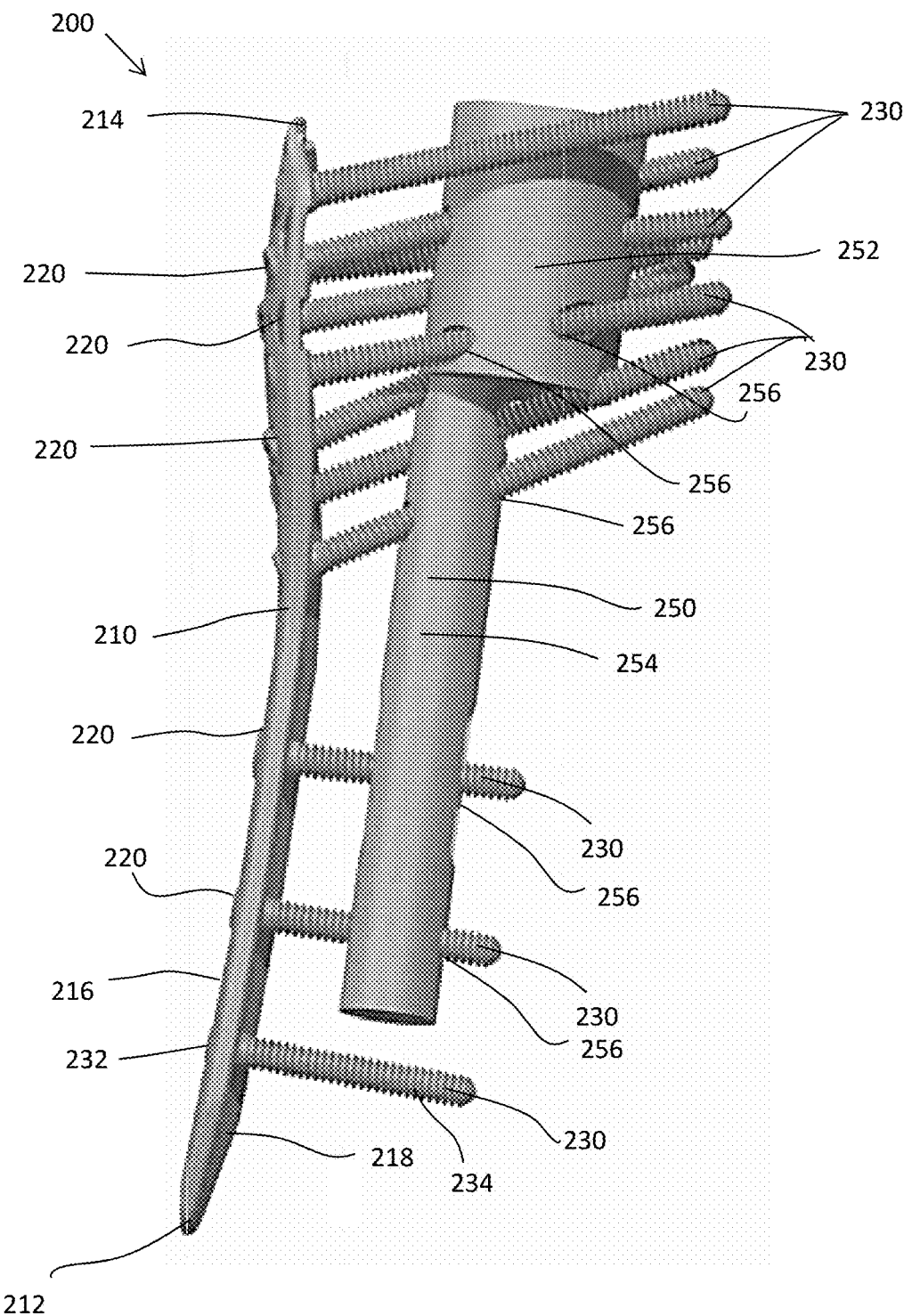
Figure 4D:
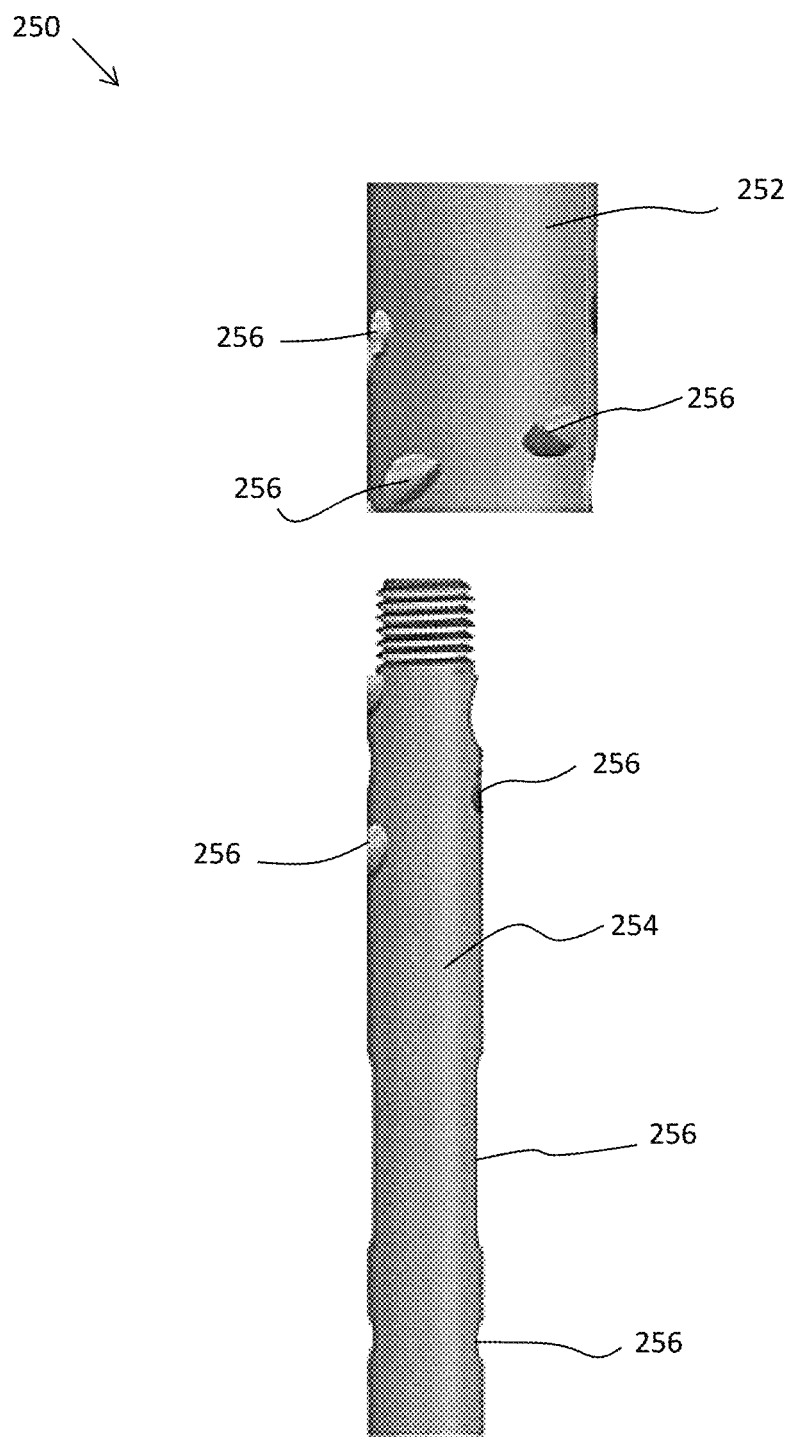
Figures 4E, 4F:
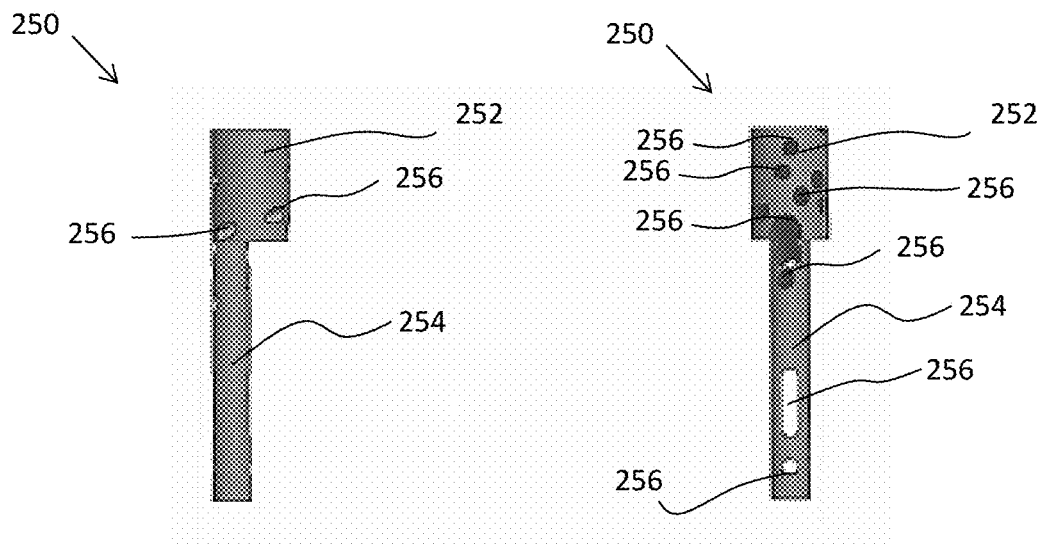

Turning now to FIGS. 4A and 4C, the proximal humerus stabilization system 200 may further include intramedullary nail 250 configured to be positioned inside the intramedullary canal of the humerus 102. It will be appreciated that the plate 210 and/or the intramedullary nail 250 may each be used alone or may be used together in combination for humeral stabilization.

The intramedullary nail 250 includes an upper portion 252 and a lower portion 254. The upper portion 252 being proximal to or configured to be positioned substantially within the humeral head 104 and the lower portion 254 being distal to the humeral head 104 and configured to extend substantially into the shaft of the humerus 102. The upper and lower portions 252, 254 may each have a width (or diameter) and a length. The width or diameter of the upper portion 252 may be greater than the width or diameter of the lower portion 254, and the length of the lower portion 254 may be greater than the length of the upper portion 252. Preferably, the upper portion 252 is sized and dimensioned to be substantially received within the humeral head 104 and the lower portion 254 is sized and dimensioned to be substantially received within the intramedullary canal.

In one embodiment, the upper portion 252 is configured as a cage, cylinder, or tube. It should be noted that the upper portion 252 may be any geometrical shape that best suits the positioning of the implant 250 within the humeral head 104. For instance, the upper portion 252 may be rectangular, oblong, polygonal, or the like. The upper portion 254 of the implant 250 may form a unitary body having a plurality of through openings or holes 256 for receiving the fasteners 230 described herein. The holes 256 may be positioned on the upper portion 252 so that the fasteners 230 enter the holes and rigidly couple the upper portion 252 to bone and/or bone fragments of the humeral head 102. Each of the plurality of holes 256 of the upper portion 252 may have an entry point and an exit point. The holes 256 may be threaded or textured (e.g., to receive locking fasteners 230) or non-threaded/non-textured (e.g., to receive compression fasteners 230).

Figures 4G, 4H:
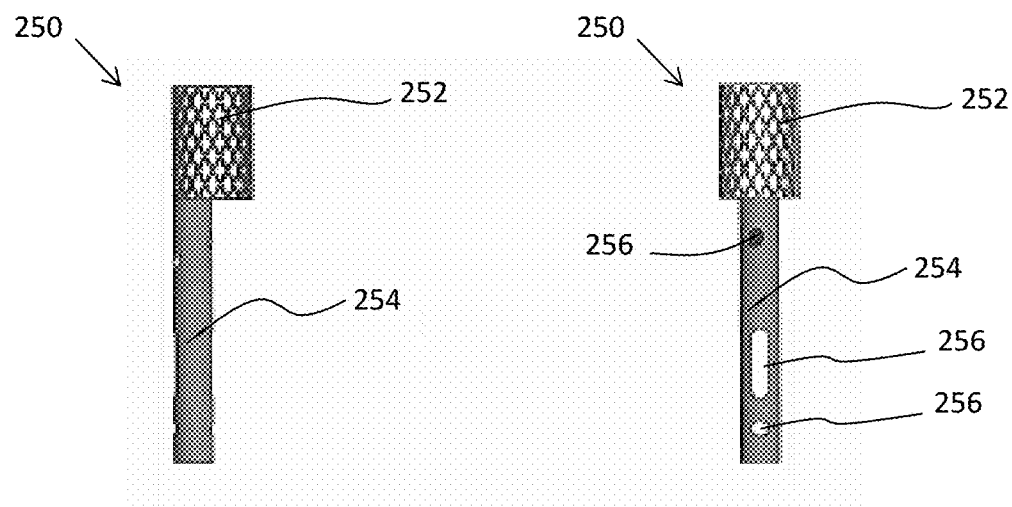

In another embodiment, the upper portion 252 may be configured having a hollow body with the plurality of holes 256 on the exterior surface of the cylinder and extending through the width or diameter of the cylinder. In another embodiment, the upper portion 252 may be configured as an expandable device, so that it enters the humeral head 104 in a first, collapsed configuration and then is expanded into a second, expanded configuration. In yet another embodiment, shown in FIGS. 4G and 4H, the upper portion 252 may be comprised of mesh or have a mesh-like surface. The cage or upper portion 252 may have a coarser mesh than the diameter of the fasteners 130 to allow screws to be passed through the mesh to lock the cage in place or the screws may be the same size or smaller and the cage may be able to deform. The mesh may be substantially rigid or may have some flexibility.

The lower portion 254 may be configured as an elongate shaft or stem. The lower portion 254 of the implant 250 may be a single body that extends from the upper portion 252 towards the distal portion of the humerus 102. The lower portion 254 may be configured as a cylindrical shaft, however, the shaft may be configured as any geometrical shape (e.g., rectangular, oblong, polygonal, or the like) that suits the intramedullary canal. The shaft or lower portion 254 may be compatible with reverse or hemi shoulder arthroplasty implants.

The lower portion 254 may form a unitary body having a plurality of through openings or holes 256 for receiving fasteners 230 as described herein. Each of the plurality of holes 256 of the lower portion 254 may have an entry point and an exit point. The holes 256 may be threaded or textured (e.g., to receive locking fasteners 230) or non-threaded/non-textured (e.g., to receive compression fasteners 230). The holes 256 in the lower portion 254 may be conical, for example, to accept polyaxial screws in the plate 210. In another embodiment, the lower portion 254 may be configured having a hollow body with the plurality of holes 256 on the exterior surface of the shaft and extending through the width or diameter of the shaft. For the locking fasteners 230, the screw heads may have optional thread in suture anchors to capture rotator cuff tendons. The lower portion 254 may have an optional hydroxyapatite (HA) coating, smooth or porous coatings. According to another embodiment, the lower portion 254 may be configured to have mesh type surface, similar or different from the mesh of the upper portion 252. According to yet another embodiment, the lower portion 254 may also be made with an expandable diameter to give surgeons greater flexibility in sizing and also facilitate distal locking, reducing typical complications.

In one embodiment, the upper portion 252 and the lower portion 254 are configured as a single, unitary body. The intramedullary implant 250 may be anatomically shaped, for example, with a range of medial bends towards the proximal head for increased support. In an alternative embodiment, shown in FIG. 4D, the upper and lower portions 252, 254 may be comprised of two separate components that may be coupled to one another, for example, through a mechanical mechanism. As shown, the lower portion 254 may include a male, threaded portion and the upper portion 252 may include a female, threaded portion (not visible) configured to receive the male, threaded portion of the lower portion 254 to couple the two parts together. The upper and lower portions 252, 254 may be coupled together by any suitable means, such as a dovetail connection, press-fit, threaded, snap-fit, or the like. In other embodiments, it should be noted that the upper portion 252 and the lower portion 254 can be exchanged and/or interchangeable to facilitate fixation of different fractures and anatomies.

According to one embodiment, the bone plate 210 may be attached to the lateral aspect of the proximal humerus 102 to fixate one or more bone fractures or fragments. The intramedullary nail 250 may be inserted into the intramedullary canal. Before or after insertion, bone graft material can be inserted or injected into the upper and/or lower portions 252, 254 of the nail 250 if desired. In addition, the distal end of the lower portion 254 may also be cemented or press fit in to the canal based on surgeon preference. One or more k-wires may be supplied through the k-wire holes 224 to assist with preliminary placement of the plate 210 and/or intramedullary nail 250. One or more sutures may be tied through the suture holes 222 to secure the plate 210 to the tissue before or after the fasteners 230 are inserted.

Pilot holes may be drilled through the fastener openings 220 to prepare to receive the respective fasteners 230. One or more drill guides may be attached to the humeral implant 250 before or during surgery to aid in insertion of lower portion 254 and/or nail 250 into the shaft of the humerus 102. The guide may be used to aim the drill for two distal screw holes. The distal screws 230 may be inserted and then the guide may be rigidly attached to the distal screws 230. The aiming arm may be disconnected from the proximal end of the nail 250. The proximal bone fragment may be placed on top of the nail 250 and the guide may be used to drill screw holes into the proximal nail 250. The screw length and size may be determined so that the articular surface is not affected. The guide may also adapt to connect to lateral platting to synchronize the hole positions.

The fasteners 230A, 230B, 230C may be positioned through the respective openings 220A, 220B, 220C in the plate 210, through the respective through holes 256 in the upper and lower portions 252, 254 of the nail 250, and into the humerus 102. The fasteners 230 may be affixed to the bone in any suitable order, number, and orientation depending on the anatomy of the bone and the fracture. In operation, each of the plurality of holes 220 of the plate 210 are positioned so that the holes 220 are geometrically are aligned with the plurality of holes 256 of the upper portion 252 and the lower portion 254 of the intramedullary implant 250. In another embodiment, the upper and lower portions 252, 254 may be designed with a degree of eccentricity so that during the implantation procedure, when the end of the lower portion 254 is rotated in the intramedullary canal, the upper portion 252 having a larger diameter, may act as a cam pushing the humeral head 104 medially into position. The plate 210 and/or intramedullary nail 250 is configured to restore the anatomic alignment and stabilize the proximal humerus 102. It is contemplated that the plate 210 may be used alone in the stabilization, the nail 250 may be used alone in the stabilization, or both the plate 210 a nail 250 may be used together in the stabilization.

The stabilization system 200 may provide the benefit of medial support to prevent collapse, ability to manipulate fragments using the device, and minimize the need for allograft, thereby decreasing biocompatibility issues. Other benefits may include minimizing the time spent shaping the fibula in the operating room, using a drill guide as a positioning arm for nail placement, and reducing negative affects to the rotator cuff. The system 200 also provides the benefit of either using or not using the lateral plate 210. When not using the lateral plate 210, the nail 250 allows for a less invasive surgical approach, helps to avoid impingement, and may increase patient comfort.

Alternative Hole Configurations

The fixed and variable angle, locking and non-locking openings 120, 220 (e.g., including openings 120A, 120B, 120C, 220A, 220B, 220C) and respective fasteners 130, 230 (e.g., including 130A, 130B, 130C, 230A, 230B, 230C) described herein may be substituted with or include one or more of the following openings 20 and/or fasteners 30, 40. The openings 20 and/or fasteners 30, 40 are generally described with reference to a generic plate 10, which may include plate 110, 210, or any other suitable plate design.

Referring now to the drawing, FIGS. 5-21 depict alternative openings 20 in plate 10. The openings 20 extending through the plate 10 are configured to accept locking fasteners 30, non-locking fasteners 40, or a combination of both locking and non-locking fasteners 30, 40 that are able to dynamically compress the bone and/or affix the plate 10 to the bone. When plating diaphyseal bone, surgeons may use a combination of both locking and non-locking fasteners 30, 40 that are able to dynamically compress bone and to connect the bone and the plate 10. Dynamic compression may also be desirable to create interfragmental compression while tightening the fasteners 30, 40.

Figure 5:
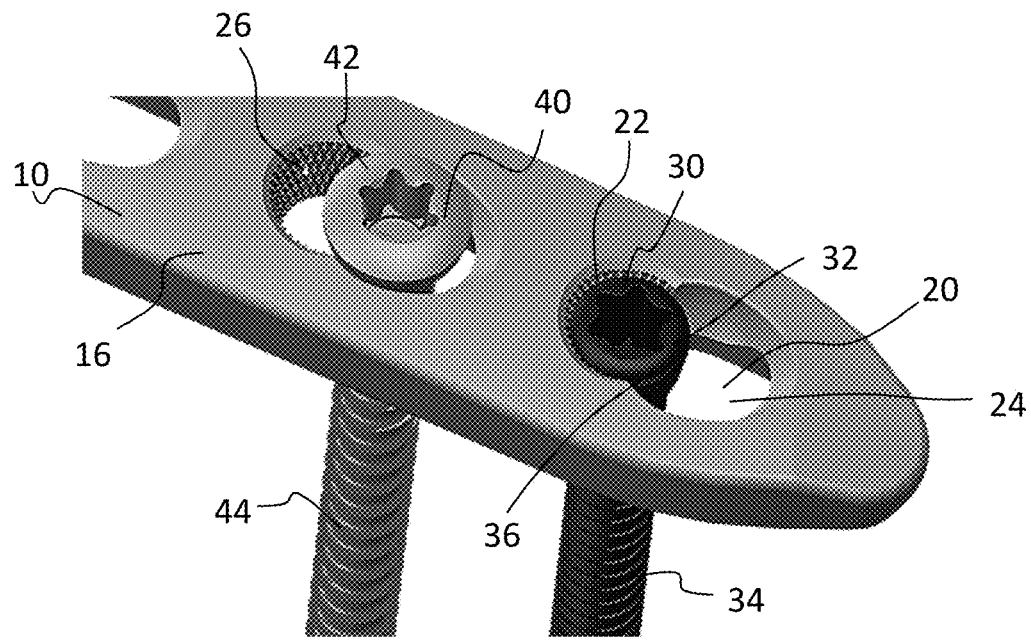
FIG. 5 is a top perspective view of two fasteners engaged with combination holes according to an embodiment.
Figure 6:
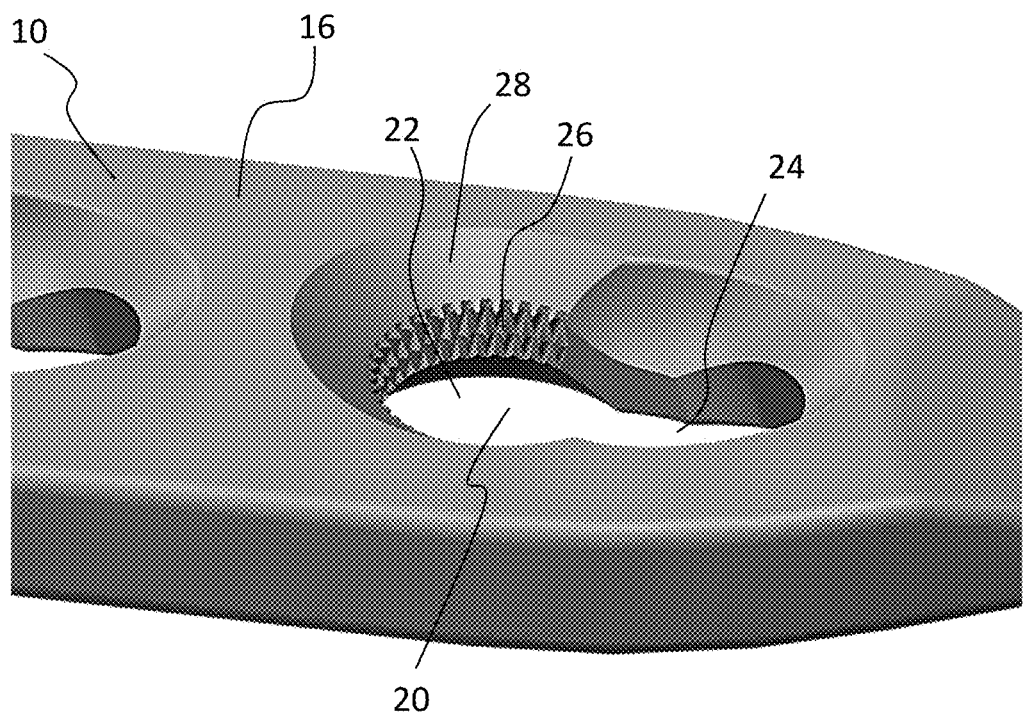
FIG. 6 is a close-up view of an alternative version of a combination hole according to another embodiment.

The plate 10 includes a top surface 16 and an opposite, bottom surface 18 configured to contact adjacent bone. The plate 10 includes one or more through openings 20 configured to receive one or more bone fasteners 30, 40. The openings 20 extend through the body of the plate 10 from the top surface 16 to the bottom surface 18. In the embodiments depicted in FIGS. 5-6, for example, the openings 20 may be in the form of a combination opening that has at least two overlapping holes. As shown in FIG. 5, the combination opening 20 includes a first hole 22 overlapping a second hole 24. One of the holes 22 may be configured to be the locking hole 22, thereby able to receive and secure the locking fastener 30 to the plate 10, and the other of the holes 24 may be configured to be the dynamic compression hole 24, thereby allowing the non-locking fastener 40 to freely move in the hole 24 and apply dynamic compression. The locking hole 22 may have one or more locking features designed to engage with a locking fastener 30, and the dynamic compression hole 24 may be elongated, for example, along the central longitudinal axis of the plate 10. The screw holes 22, 24 are not constrained to parallel axes. This hole geometry may be used in bone plates 10 to utilize either fixed angle or variable angle locking screws 30 and/or polyaxial non-locking screws 40 that can achieve dynamic compression.

These openings 20 allow surgeons more flexibility for fastener placement, based on preference, anatomy, and fracture location. Surgeons may have differing opinions as to whether non-locking or locking screws 30, 40 (or some combination of the two) should be used in diaphyseal bone. Further, complexity of fracture location and shape makes having as many locations for fasteners 30, 40 as possible necessary. This design offers surgeons a versatile method to achieve higher accuracy in placement of locking and/or non-locking screws 30, 40.

As best seen in FIG. 5, the locking and non-locking fasteners 30, 40 are shown. The locking and non-locking fasteners 30, 40 may include traditional fasteners known in the art. The locking and non-locking fasteners 30, 40 may comprise bone screws or the like. The fasteners 30, 40 may also include other fasteners or anchors configured to be secured or engaged with bone, such as nails, spikes, staples, pegs, barbs, hooks, or the like. The fasteners 30, 40 may include fixed and/or variable angle bone screws.

The locking fastener 30 may include a head portion 32 and a shaft portion 34 configured to engage bone. The shaft portion 34 may be threaded such that the fastener 30 may be threaded into the bone. The head portion 32 of the locking fastener 30 includes a textured area 36 around its outer surface sized and configured to engage with the locking hole 22 of the combination opening 20. The textured area 36 may include threads, ridges, bumps, dimples, serrations, or other types of textured areas. As shown, the texture area 36 preferably includes a threaded portion extending substantially from the top of the head portion 32 to the bottom of the head portion 32 proximate to the shaft portion 34. Thus, when the textured area 36 engages the locking hole 22, the locking fastener 30 is thereby locked to the plate 10.

The non-locking fastener 40 includes a head portion 42 and a shaft portion 44 configured to engage bone. The shaft portion 44 may be threaded such that the fastener 40 may be threaded into the bone. The head portion 42 of the non-locking fastener 40 is substantially smooth around its outer surface such that is able to slide along the elongated compression hole 24. Thus, the non-locking fastener 30 may be coupled to the plate 10, but not locked thereto to enable dynamic compression of the bone. It will be recognized that the head portions 32, 42 of the fasteners 30, 40 may include a recess configured to receive a driver or the like.

The locking hole portion 22 of the combination opening 20 includes a textured portion 26. The textured portion 26 may include threads, ridges, bumps, dimples, serrations, knurls, or other types of textured areas. The textured portion 26 may be of the same type (e.g., mating surfaces) or different from the textured area 36 of the locking fastener 30. As shown, the textured portion 26 is serrated or knurled along an inner portion of the hole 22. The knurled surface may include straight, angled, or crossed lines cut or rolled into the material. In the embodiment shown in FIG. 5, the textured portion 26 extends along substantially the entire inner surface of the hole 22. With reference to the embodiment shown in FIG. 6, the combination hole 20 is substantially the same as that shown in FIG. 5 except that the textured portion 26 the locking hole 22 now includes a thin centralized textured ribbon of material. For example, the textured portion 26 takes up about half or less of the surface area of the hole 22. In this instance, only a portion of the textured area 36 of the head portion 32 of the locking fastener 30 engages with and locks to the textured portion 26 of the hole 22.

An upper portion of the hole 22 may be tapered 28, without texturing, for example, to facilitate alignment of the fastener 30 with the opening 20. As shown in FIG. 7, this tapered portion 28 is enlarged in area relative to the embodiment in FIG. 5. The hole 22 may be configured to receive a fixed or variable angle fastener 30. The hole 22 may be generally conical in shape such that it is wider near the top surface 16 of the plate 10 and narrower toward the bottom surface 18 of the plate 10. The tapered portion 28 and/or the textured area 26 may be conical in shape. In this embodiment, the locking hole 22 is a textured fixed angle conical hole configured to receive locking fastener 30. The textured holes 22 may deform as the fastener head 32 interferes with the textured portion 26 of the hole 22, thereby providing a positive lock between the fastener 30 and the plate 10.

The second hole portion 24 of the combination opening 20 may be an elongated dynamic compression hole. The dynamic compression hole 24 may be elongated such that it has a length greater than its width. The hole 24 may be elongated along the longitudinal axis of the plate 10. In the alternative, the hole 24 may be generally cylindrical such that the hole 24 only permits polyaxial movement of the fastener 40. The inner surface of the hole 24 may be substantially smooth such that the non-locking fastener 40 is able to freely pivot and/or slide along the hole 24. This provides for at least two directions of compressive force (e.g., along the longitudinal axis and perpendicular to the longitudinal axis of the plate 10). The head portion 42 of the non-locking fastener 40 may be substantially smooth around its outer surface. The head portion 42 is sized and configured to engage with and be retained within the hole portion 24 of the combination opening 20. The hole 24 may be configured to receive a fixed or variable angle fastener 40. In one embodiment, the hole 24 may be generally conical in shape and/or tapered such that it is wider near the top surface 16 of the plate 10 and narrower toward the bottom surface 18 of the plate 10. In this embodiment, the hole 24 is a smooth variable angle conical hole configured to receive the non-locking fastener 40. The hole 24 may receive the fastener head 42 allowing movement of the fastener 40, for example, in a polyaxial fashion and/or along the length of the hole 22, thereby providing dynamic compression of the bone.

Turning now to FIGS. 7-13, alternative types of openings 20A-20G, which provide for locking and/or non-locking, dynamic compression are provided. As many of the features of these openings are similar to the combination openings 20 described already for FIGS. 5-6, only the different features will be further explained.

Figure 7A:
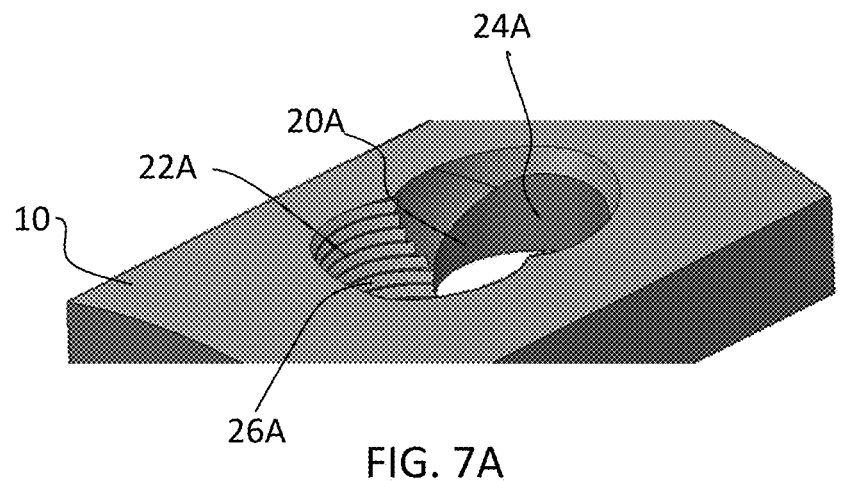
FIGS. 7A-7C show a perspective view, top view, and cross-section view, respectively, of an another embodiment of a combination hole.
Figure 7B:
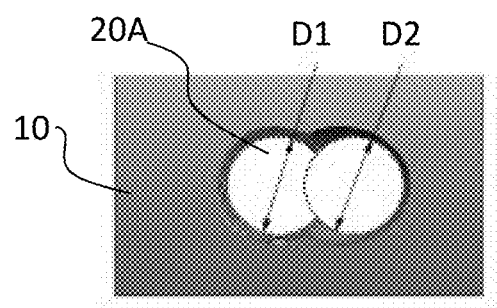
Figure 7C:
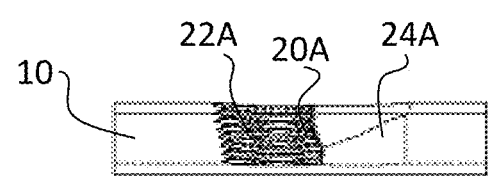

With reference to FIGS. 7A-7C, the combination opening 20A is similar to combination opening 20 except that the dynamic compression hole 24A has the same general diameter as the locking hole 22A, and the locking hole 22A includes a different type of textured portion 26A. In this embodiment, the locking hole 22A has a first diameter D1, and the dynamic compression hole 24A has a second diameter D2. Unlike the elongated hole 24 described earlier, dynamic compression hole 24A has substantially same diameter as the locking hole 22A. Thus, the first and second diameters D1, D2 are substantially the same. The hole 24A may be formed by milling or drilling a sphere out of the plate 10 in the center of the circle with tapers or ramps on either side. The hole 24A is not elongated, but is generally circular and the non-locking fastener 40 will be allowed to translate in the hole 24A because the diameter of the head portion 42 and/or shaft (e.g., bone thread) will be smaller than the size of the hole 24A in the plate 10. With respect to hole 22A, the textured portion 26A of the hole 22A may be in the form of a tapered thread. This tapered thread may generally correspond to a similar tapered thread on the locking fastener 30. This hole 22A also does not include a tapered portion, and the textured portion 26A begins at the intersection with the top surface 16 of the plate 10. This alternative opening 20A also provides for the use of both locking and non-locking fasteners 30, 40 that are able to dynamically compress bone and/or lock the plate 10 to the bone.

Figure 8A:
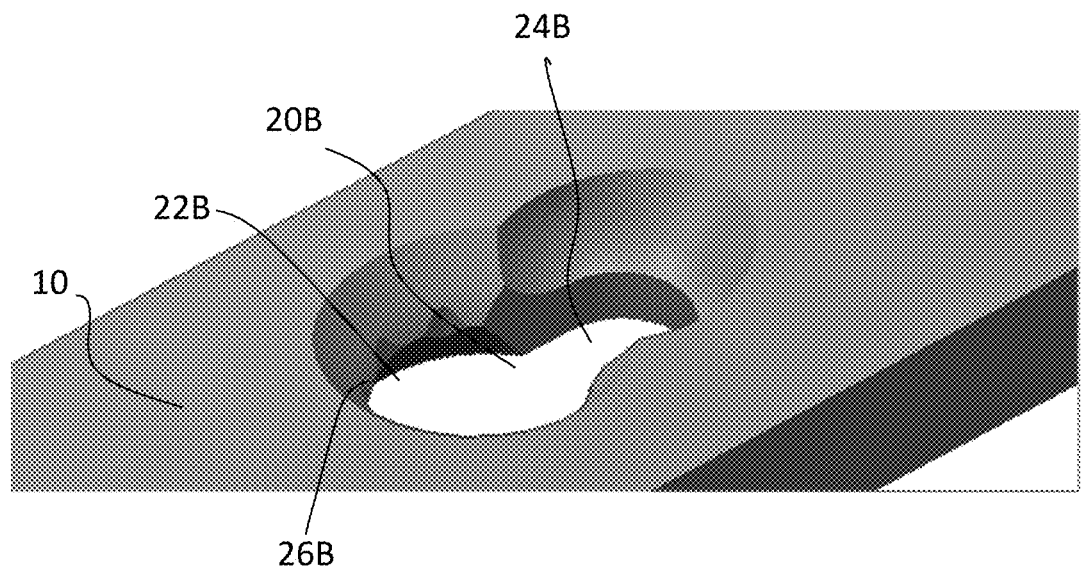
FIGS. 8A-8C show a perspective view, top view, and cross-section view, respectively, of an another embodiment of a combination hole.
Figure 8B:
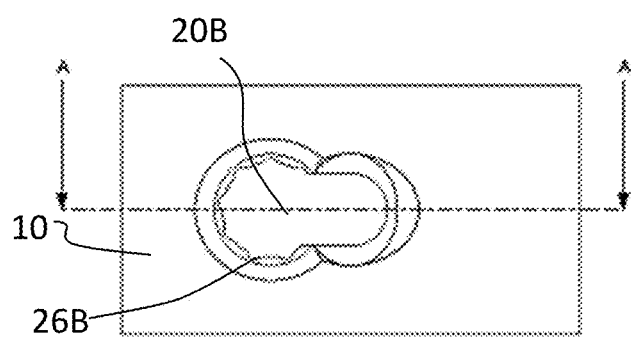
Figure 8C:
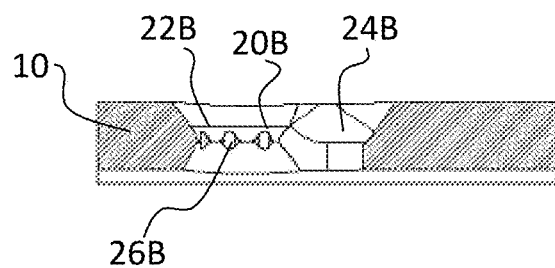

Turning now to FIGS. 8A-8C, the combination opening 20B is similar to other combination openings except that the locking hole 22B includes a different type of textured portion 26B. The textured portion 26B includes a series of alternating recesses and protrusions around a central portion of the hole 22B. The recesses may be in form of a wave of alternating cutouts extending around the inner perimeter of the hole 22B. The textured portion 26B may lock the fastener 30 with a friction fit or may be modified during insertion of the fastener 30 to form a lock in situ. In this embodiment, the locking hole may allow for polyaxial locking. The plate 10 and the locking fastener 30 may be made of dissimilar materials having dissimilar hardness values. For example, the fastener 30 may have a higher hardness (e.g., on the Rockwell scale) relative to the plate 10, which may be formed of a material having a lower relative hardness value. Due to the increased hardness, the head portion 32 of the locking fastener 30 may create a thread in the plate 10 as the fastener 30 is inserted (e.g., threaded) into the hole 22B, thereby locking the fastener 30 to the plate 10.

Figure 9A:
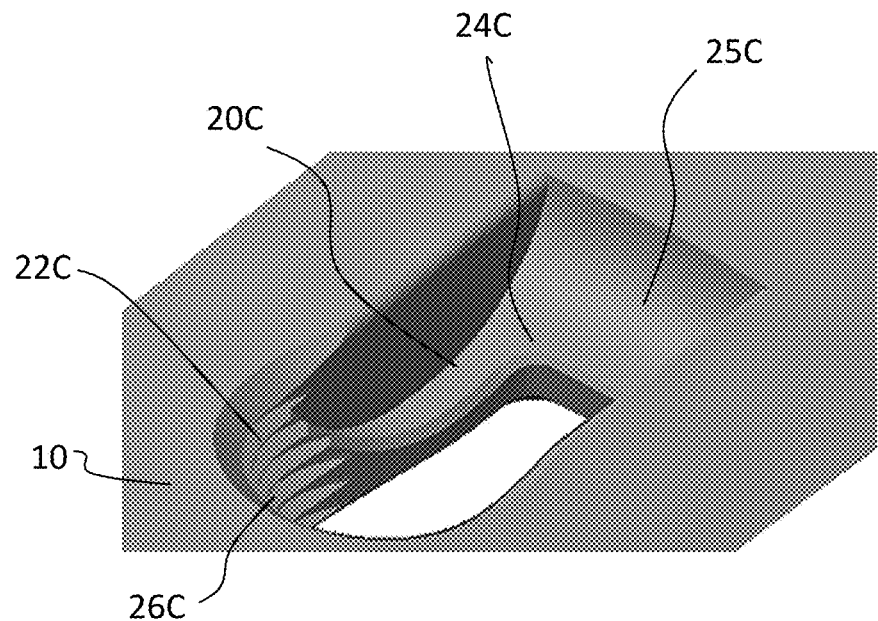
FIGS. 9A-9C show a perspective view, top view, and cross-section view, respectively, of an another embodiment of a hole for receiving a fastener.
Figure 9B:
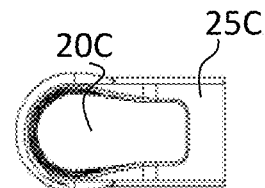
Figure 9C:
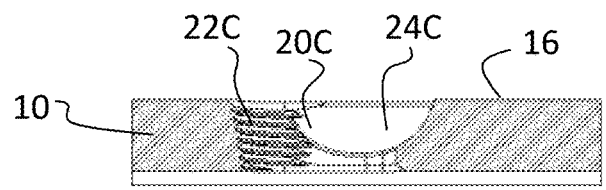

With reference to FIGS. 9A-9C, the opening 20C includes locking hole 22C and dynamic compression hole 24C with a more open configuration. The locking portion 22C has a textured portion 26C in the form of a tapered thread. This tapered thread may generally correspond to a similar tapered thread on the locking fastener 30. The opposite portion 24C of the opening 20C is oblong with a ramp 25C milled into the top surface 16 of the plate 10 to allow for dynamic compression. As best seen in FIG. 9C, the ramp may be partially spherical in shape and extend from the top surface 16 of the plate 10 and connect to the textured portion 26C. When viewed from above in FIG. 9B, the ramp 25C creates a square-like, key-hole, and/or non-hole geometry that sweeps into the tapered threaded locking hole 22C. This alternative opening 20C also provides for the use of both locking and non-locking fasteners 30, 40 that are able to dynamically compress bone and/or lock the plate 10 to the bone.

Figure 10A:
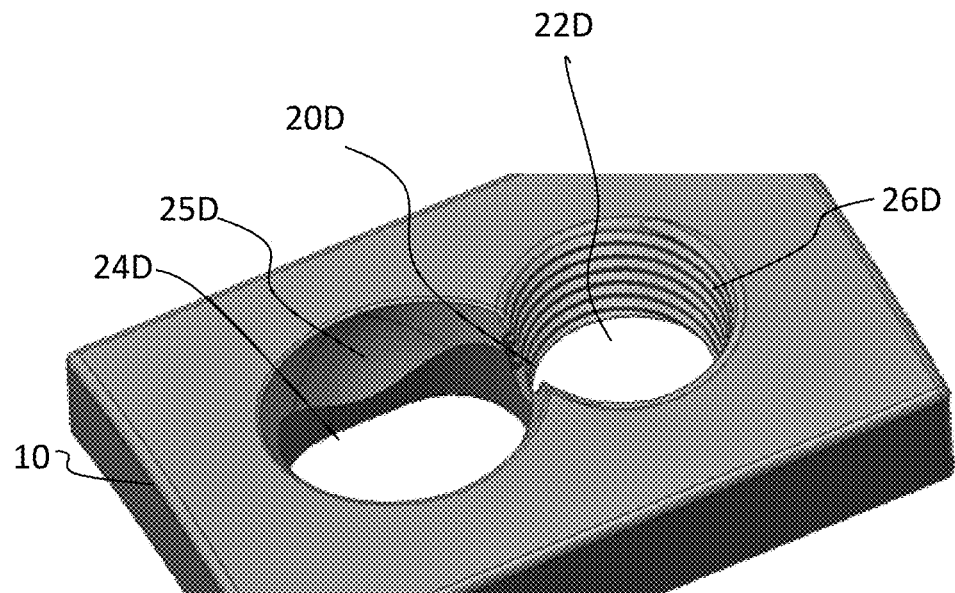
FIGS. 10A-10C show a perspective view, top view, and cross-section view, respectively, of an another embodiment of a combination hole.
Figure 10B:
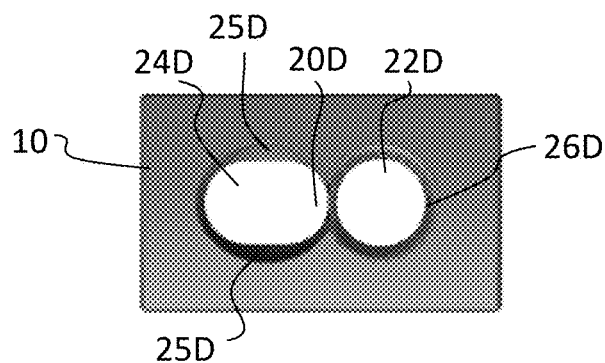
Figure 10C:
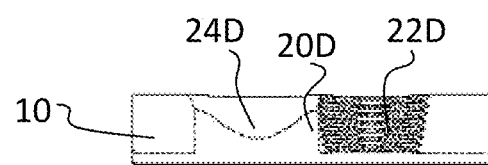

Turning now to FIGS. 10A-10C, the opening 20D includes locking hole 22D and dynamic compression hole 24D. These holes 22D, 24D are connected and close together but are not overlapping. The holes 22D, 24D are separated by a small portion or sliver of plate material proximate to the lower portion of the holes 22D, 24D (e.g., at bottom surface 18 of the plate 10 and partially extending between the holes 22D, 24D). The locking portion 22D has a textured portion 26D in the form of a tapered thread. The textured portion 26D extends around almost the entire circumference of the hole 22D except where connected to hole 24D. The dynamic compression hole 24D is elongated and has ramped portions 25D on opposite sides of the hole 24D to receive fastener 40. This configuration allows for a very close population of holes 22D, 24D on the plate 10 while giving structural stability at the holes 22D, 24D.

Figure 11A:
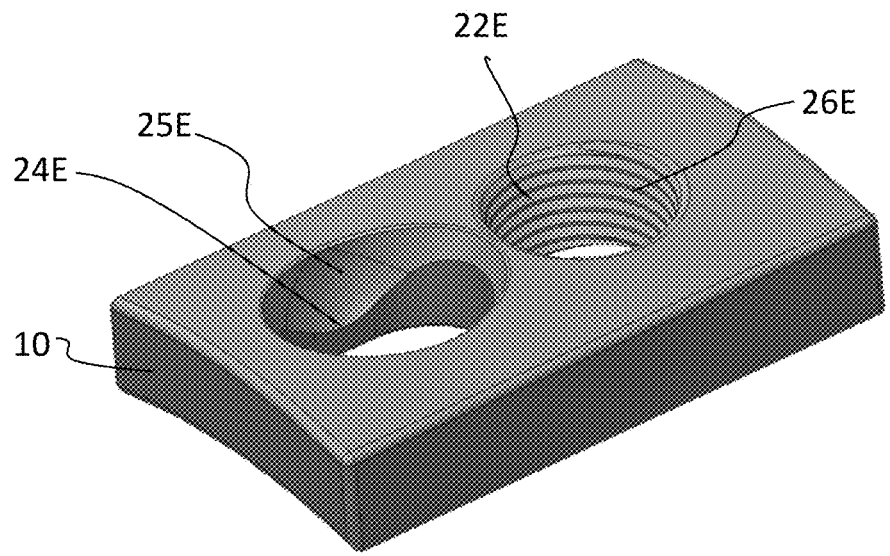
FIGS. 11A-11C show a perspective view, top view, and cross-section view, respectively, of an another embodiment of separate locking and non-locking holes.
Figure 11B:
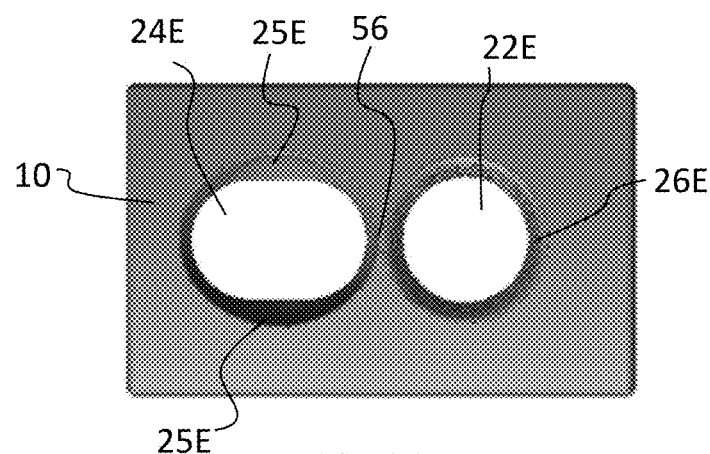
Figure 11C:
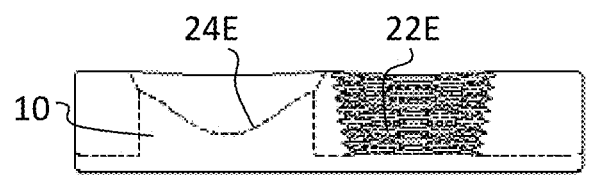

With reference to FIGS. 11A-11C, locking hole 22E and dynamic compression hole 24E are adjacent, but separate from one another. The holes 22E, 24E are completely separated from one another by a wall 56 of plate material. The locking portion 22E has a textured portion 26E in the form of a tapered thread extends around the entire perimeter of the hole 22E. The dynamic compression hole 24E is elongated and has ramped portions 25E on opposite sides of the hole 24E. This configuration also allows for a very close population of holes 22E, 24E on the plate 10 while giving options for both locking and/or dynamic compression.

Turning now to FIGS. 12A-12D, an alternative version of opening 20F is provided. In this embodiment, the hole construct 20F is comprised of at least three overlapping conical threaded holes in the plate 10. The opening 20F includes a first, locking hole 22F, a second hole 24F, and a third hole 23F arranged along a longitudinal axis of the plate 10. The third hole 23F is the mirror image of hole 24F across the first locking hole 22F. The conically threaded holes 22F, 23F, 24F may or may not have parallel axes. Each hole 22F, 23F, 24F may include a textured portion 26F, for example, in the form of one or more threaded portions. Thus, the locking fastener 30 may lock to any of the holes 22F, 23F, 24F. Although each of the holes 22F, 23F, 24F are shown in with the textured portion 26F, it will be appreciated that one or more of the holes 22F, 23F, 24F may have a substantially smooth inner portion instead of the textured portion 26F. The upper part of the hole construct at the first and second ends of the hole 20F each have a ramped feature 25F (e.g., adjacent to holes 23F and 24F) to allow for dynamic compression of the plate 10. In addition, the ramped feature 25F may span the three or more conical holes 22F, 23F, 24F (e.g., around the entire perimeter of the opening 20F).

Figure 12A:
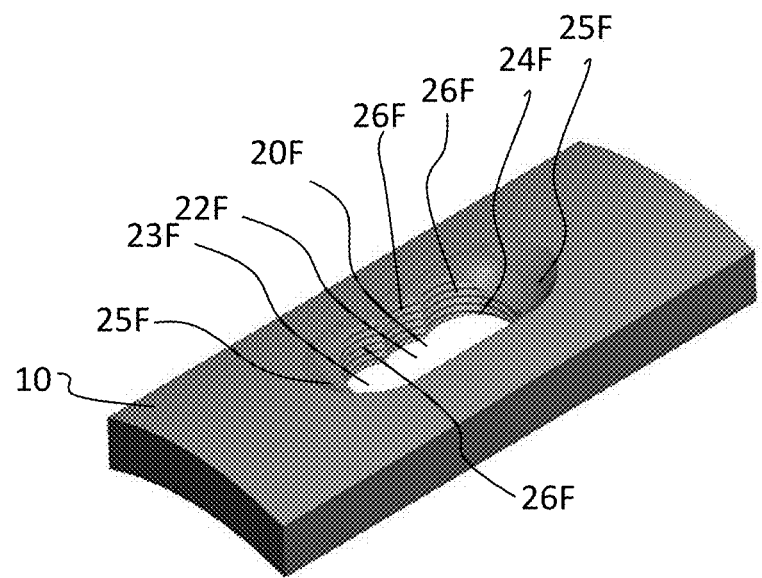
FIGS. 12A-12D show a perspective view, a top view, a cross-section view, and a perspective view with a locking fastener, respectively, according to another embodiment of a plate including three overlapping locking and non-locking holes.
Figure 12B:
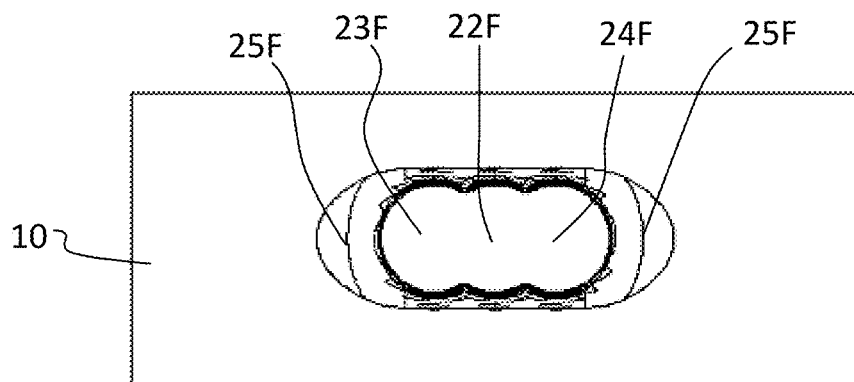
Figure 12C:
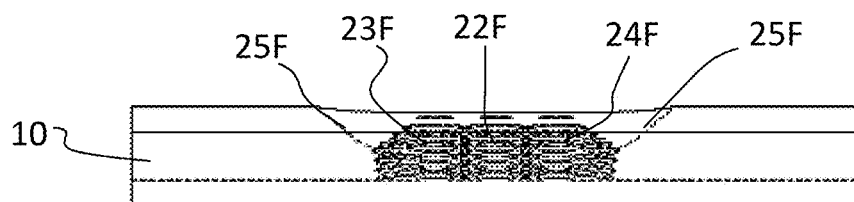
Figure 12D:
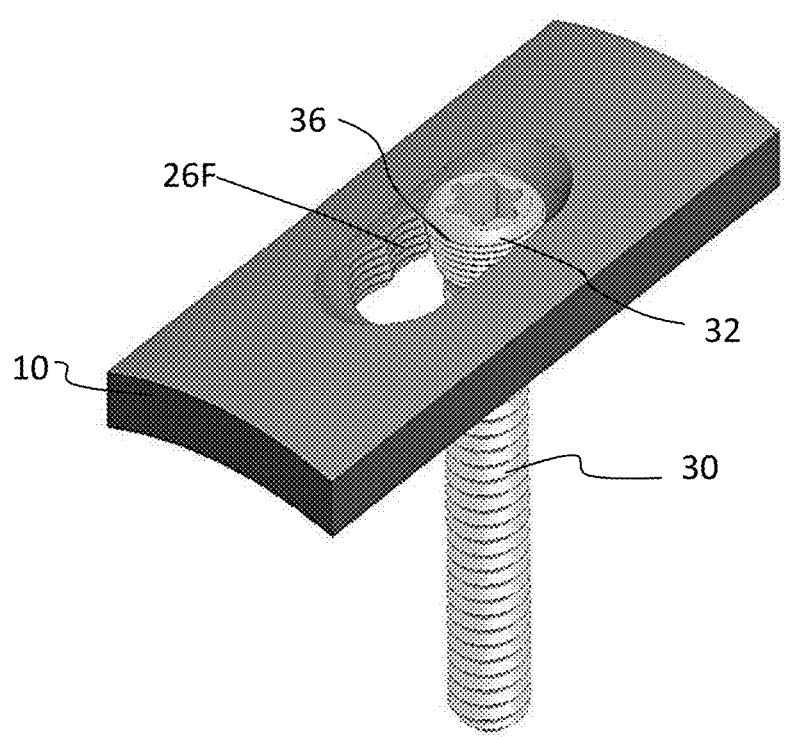

The non-locking compression fasteners 40 may have a major bone thread diameter such that the fastener 40 can translate between overlapping holes 22F, 24F, 23F without interference. As best seen in FIG. 12D, the locking fastener 30 may include a textured area 36, for example, in the form of a thread, configured to engage with the textured portion 26F of any of the holes 22F, 23F, 24F. The hole geometry of opening 20F can be applied to bone plates 10 to utilize either fixed angle and/or variable angle locking screws 30 and/or polyaxial non-locking screws 40 that can achieve dynamic compression. This allows surgeons more flexibility for screw placement, based on preference, anatomy, and fracture location.

Figure 13A:
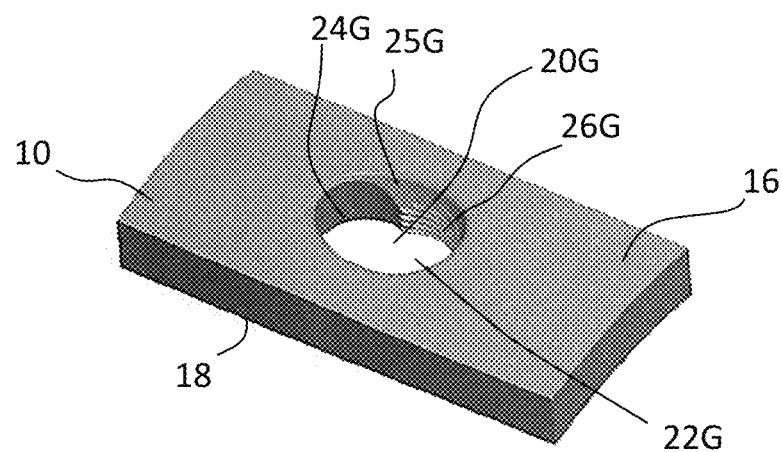
FIGS. 13A-13B show perspective views of a plate according to another embodiment with locking and non-locking functionality.
Figure 13B:
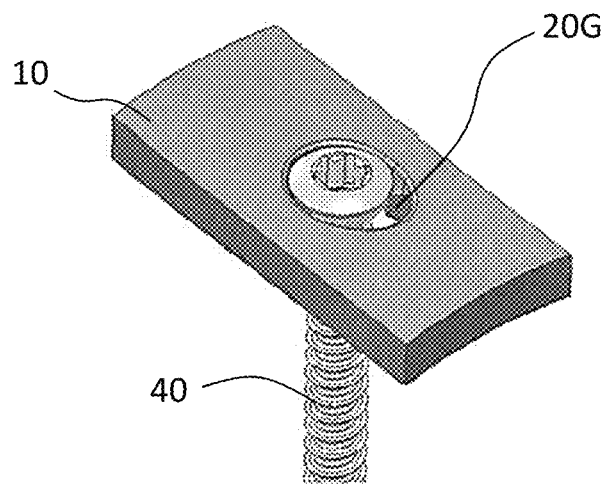

Turning now to FIGS. 13A-13B, another embodiment of opening 20G is provided. This opening 20G may be comprised of one elongate hole or slot extending from the top surface 16 to the bottom surface 18 of the plate 10. A locking portion 22G of the opening 20G may include a textured portion 26G having straight machine threads. The threads may extend more than 180 degrees to retain the locking fastener 30. A non-locking portion 24G of the opening 20G may be positioned opposite the locking portion 22G to complete the opening 20G. The upper part of the opening 20G may have one or more ramped features 25G to allow for dynamic compression of the plate 10. The ramp 25G may span along the entire upper perimeter of the elongated slot 20G or a portion thereof. The compression screws 40 may have a major bone thread diameter such that the screws 40 are able to translate along the opening 20G without interference.

With reference to FIGS. 14A-14E, alternative embodiments of the locking fastener 30 may be used with any plate 10. The head portion 32 of the fastener 30 may include a textured area 36 in the form of a thread, for example, to lock the fastener 30 to the plate 10. The fastener 30 and/or plate 10 may also include one or more mechanisms to prevent back out of the fastener 30 from the plate 10. In FIG. 14A, the head portion 32 includes at threaded portion 36A (e.g., having straight threads) that interface with the plate 10 and the top of the head extends larger than the threads. The head portion 32 bottoms out when the fastener 30 is fully inserted and creates preload in the fastener 30, thus locking the fastener 30 rotationally. In FIG. 14B, the head portion 32 includes threaded portion 36B. The head portion 32 has a constant major diameter while the minor diameter is tapered. The thread depth may go to zero at the top of the head portion 32 of the screw 30. The first few turns smoothly insert, but as the tapered portion of the male thread engages with the plate 10, interference occurs, jamming and/or locking the screw 30 and preventing backout. In FIG. 14C, a screw thread 36C on the head portion 32, similar to the design in FIG. 14B, except the minor diameter of the screw 30 stays constant while the major diameter of the head portion 32 gets larger toward the top of the screw 30. A similar jamming and locking mechanism results through tightening of the screw 30 in the plate 10. In FIG. 14D, the threaded portion 36D has areas of varying pitch. In particular, a straight screw thread on the head portion 32 of the screw 30 has a similar pitch to that of the plate 10 at the bottom of the head portion 32 of the screw 30. The pitch then increases or decreases towards the top of the head portion 32, which thereby results in jamming of the threads and preventing unwanted backout of the screw 30. In an alternative variation of the concept of FIG. 14D, shown in FIG. 14E, the opening in the plate 10 is provided with areas of varying pitch while the pitch of the threaded portion 36D remains constant. For example, the head portion 32 may include a straight thread with a constant pitch. The upper surface of the plate 10 may include a thread pitch is similar to that of the screw 10, but towards the bottom surface of the plate 10, the thread pitch would either increase or decrease to lock the screw 30 to the plate 10.

Figure 15A:
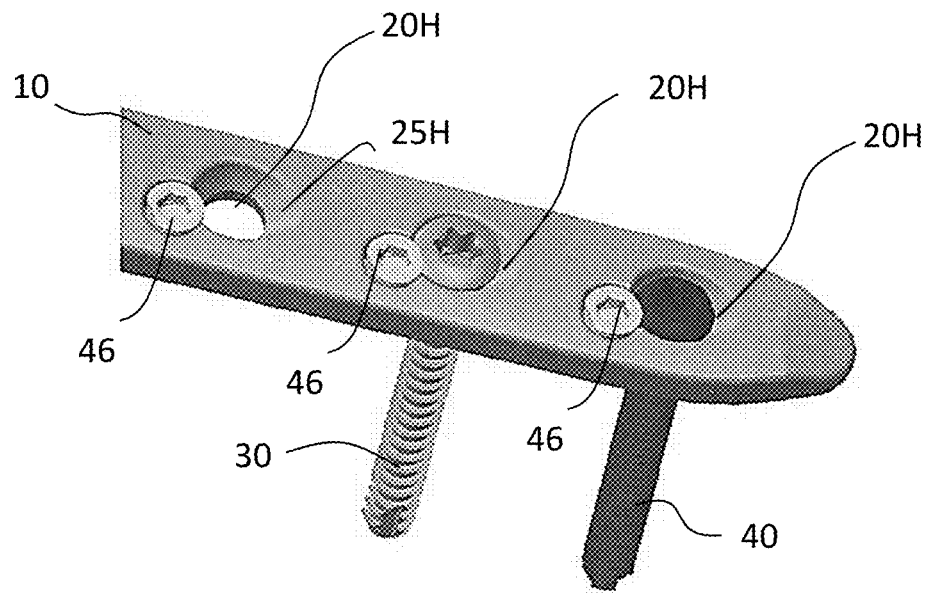
FIGS. 15A and 15B depict a perspective view and cross-section view of an alternative version of a plate with blocking screws.
Figure 15B:
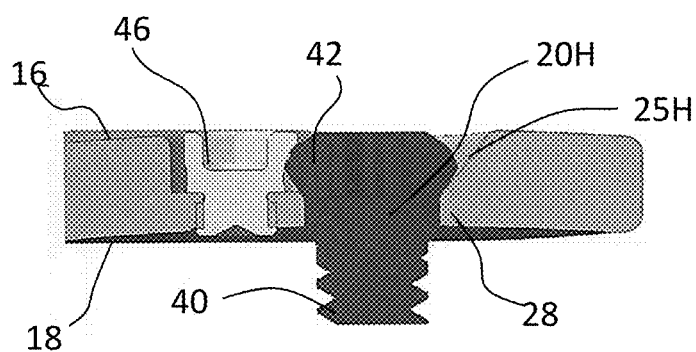

Turning now to FIGS. 15A and 15B, the plate 10 includes an additional anti-backout feature. In this embodiment, the plate 10 includes cylindrical holes or openings 20H configured to accept either the compression fastener 40 or the locking fastener 30. Each opening 20H may include a ramped portion 25H extending around a portion or the entire perimeter of the opening 20H to allow for dynamic compression with a compression fastener 40. Each opening 20H may include a cylindrical feature to provide angular stability with a locking fastener 30. The opening 20H may also include an angular taper 28 to cause compressive tightening between the locking fastener 30 and the cylindrical opening 20H. Each opening 20H has an accompanying blocking screw 46 that can be actuated to block the fastener 30, 40 from backing out. The blocking screw 46 may extend from a first end at the top surface 16 to a second end at the bottom surface 18 of the plate 10. The first end of the blocking screw 46 may include a recess sized to receive an instrument to rotate the blocking screw 46 from an unblocked position to a blocked position. The blocked position may include a portion of the blocking screw 46 covering a portion of the head portion 42 of the fastener 40, thereby further preventing backout of the fastener 40 from the plate 10.

According to yet another embodiment, the plate 10 may include one or more openings 20 configured to receive the locking fastener 30 having self-forming threads that work by displacement of the plate material to lock the fastener 30 to the plate 10. Turning now to FIGS. 16-21, the locking fastener 30 and alternative embodiments of the openings 20 in the plate 10 are shown. In these embodiments, the locking mechanism of the fastener 30 (e.g., bone screw) to the internal fixation plate 10 may allow for variable angle screw insertion. The fastener 30 may be inserted within an angular cone where the force required to dislodge the head portion 32 of the fastener 30 is substantially equivalent to the force required when the fastener 30 is inserted perpendicular to the plate 10. The holes or openings 20 in the plate 10 may be shaped such that the fastener 30 may be inserted at different angles. The geometry of the opening 20 is conducive to catching the threads on the head portion 32 of the fastener 30 and to reduce the axial force necessary to initiate the thread formation.

The locking mechanism includes a fastener 30 having a head portion 32 with self-forming threads that displace the plate material. The plate 10 may be made of a material softer than the fastener 30 to facilitate displacement. For example, the plate 10 may be comprised of titanium, alloys, polymers, or other materials having a lower material hardness (e.g., Rockwell hardness). The fastener 30 may be made of a harder relative material, for example, comprised of cobalt chrome, tungsten, alloys, or other materials having a higher material hardness. Preferably, the fastener 30 is comprised of a material having a strong, stiff, and high surface hardness which facilitates the thread forming process. The forming mechanism works by displacement of material rather than removal of the material of the plate 10, thereby minimizing fragments or chips which are created from tapping.

Figure 16A:
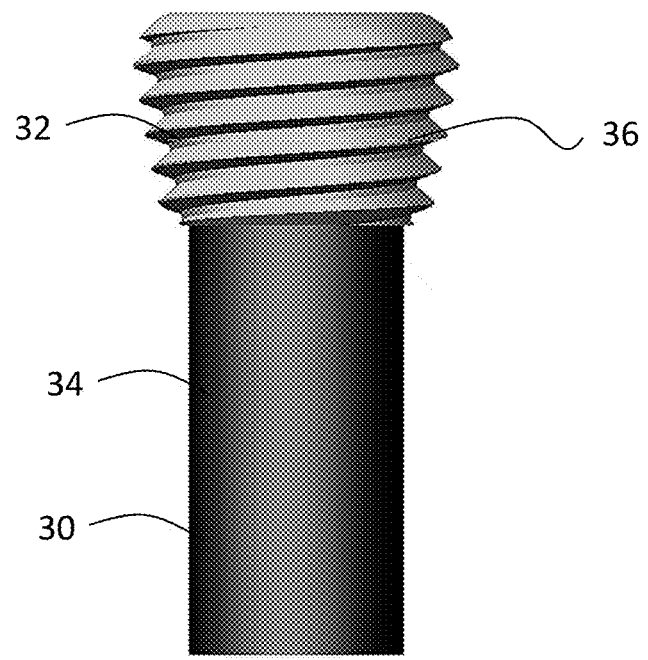
FIGS. 16A and 16B depict a fastener according to another embodiment with self-forming threads configured to form threads in the opening of a plate.
Figure 16B:
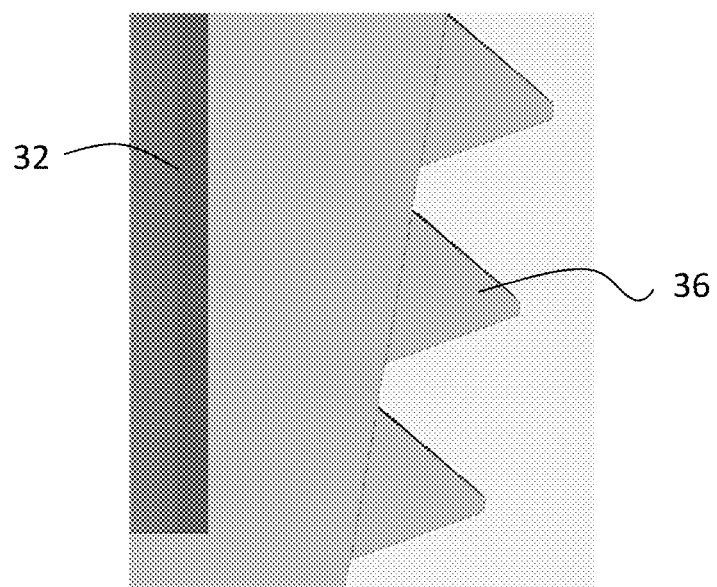
Figure 17A:
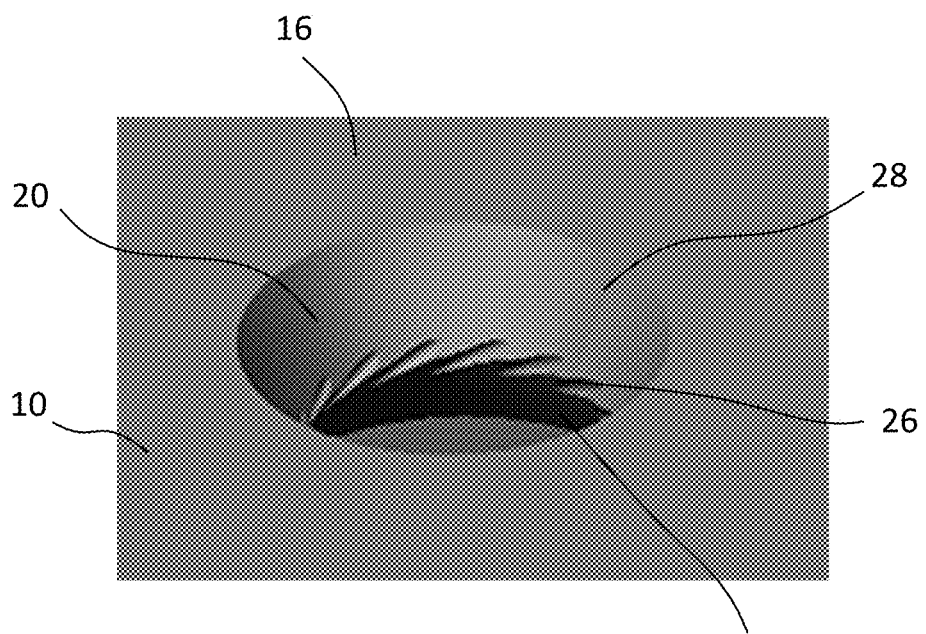
FIGS. 17A and 17B depict an opening in a plate according to one embodiment having a windswept cut configured to receive the self-forming threads of the fastener of FIGS. 16A-16B.
Figure 17B:
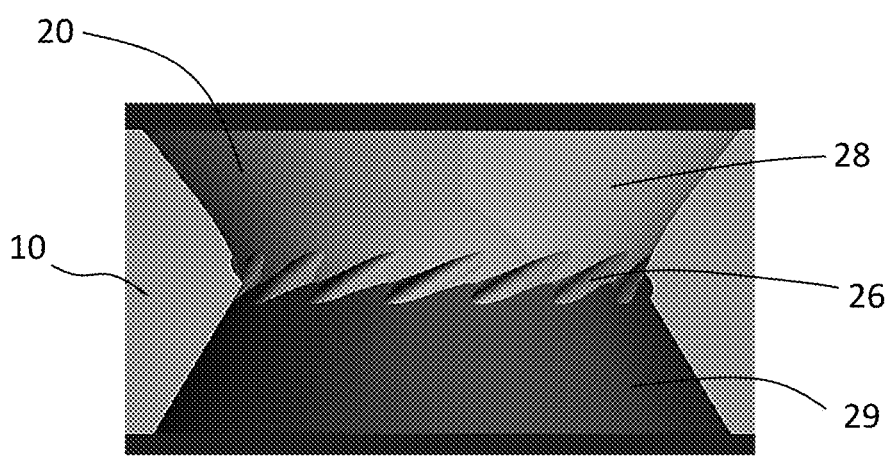

In FIGS. 16A-16B, the locking fastener 30 includes a head portion 32 and a shaft portion 34 configured to engage bone. Although not shown, the shaft portion 34 may be threaded such that the fastener 30 may be threaded into the bone. The head portion 32 may be tapered (e.g., at an angle of about 20°) such that the fit within the opening 20 in the plate 10 becomes tighter as the fastener 30 is advanced in to the bone. The head portion 32 of the locking fastener 30 includes a textured area 36 around its outer surface sized and configured to engage an opening 20 in the plate 10. The textured area 36 may include threads, ridges, bumps, dimples, serrations, or other types of textured areas. As shown, the textured area 36 preferably includes a threaded portion extending substantially from the top of the head portion 32 to the bottom of the head portion 32 proximate to the shaft portion 34. The threads 36 may run generally perpendicular to the conical surface of the head portion 32. The threaded portion 36 is in the form of self-forming threads configured to displace the plate material and create threads in the opening 20 of the plate 10. The threaded portion has an exaggerated sharp thread peak to facilitate cutting or forming of the plate material.

Turning now to FIGS. 17A-20B, alternative versions of the openings 20 are shown before being tapped with the fastener 30. Once the fastener 30 is inserted, these openings 20 are modified based on the self-forming threads. The geometry of the openings 20 are conducive to catching the threads 36 and designed to reduce the axial force necessary to initiate the thread formation. An upper portion of the hole 20 may be tapered 28, for example, with a conical straight tapered surface cut through the top surface 16 of the plate 10 for clearance of the head portion 32 of the fastener 30 during off angle insertion. A lower portion of hole 20 may further be tapered 29, for example, with a conical straight tapered surface cut through the bottom surface 18 of the plate 10 for clearance of the shaft portion 34 during off angle insertion. The upper tapered portion 28 may be larger, for example, with a larger degree of taper than the lower tapered portion 29. For example, the upper tapered portion 28 may have a taper in a range from about 60-90°, 70-80°, or 72-78°, preferably about 70°, 75°, or 80° whereas the lower tapered portion 29 may have a taper in a range from about 50-70°, 55-65°, or 57-63°, preferably about 55°, 60°, or 65°. The upper and/or lowered tapered portions 28, 29 may be substantially conical (e.g., FIGS. 17B, 18B, 19B) or may be segmented with more than one section, such as two separate conical sections having different diameters or degrees of taper (e.g., FIGS. 20A and 20B).

At the intersection between the upper tapered portion 28 and the lower tapered portion 29 a narrowed central portion may have a textured portion 26. As described herein, the textured portion 26 may include threads, ridges, bumps, dimples, serrations, or other types of textured areas. In the embodiment shown in FIGS. 17A-17B, the textured portion 26 includes a windswept cut design comprised of a plurality of shallow cuts where each cut overlaps the next. For example, the windswept design may include a plurality of threadlike helical cut sweeps. Each cut has a smooth transition into the inner diameter of the hole 20 (e.g., into the upper and lower tapered portions 28, 29). The windswept cuts provide a positive surface for the self-forming threads to cut into, thereby helping to prevent peeling of the newly formed threads into the plate 10.

Figure 18A:
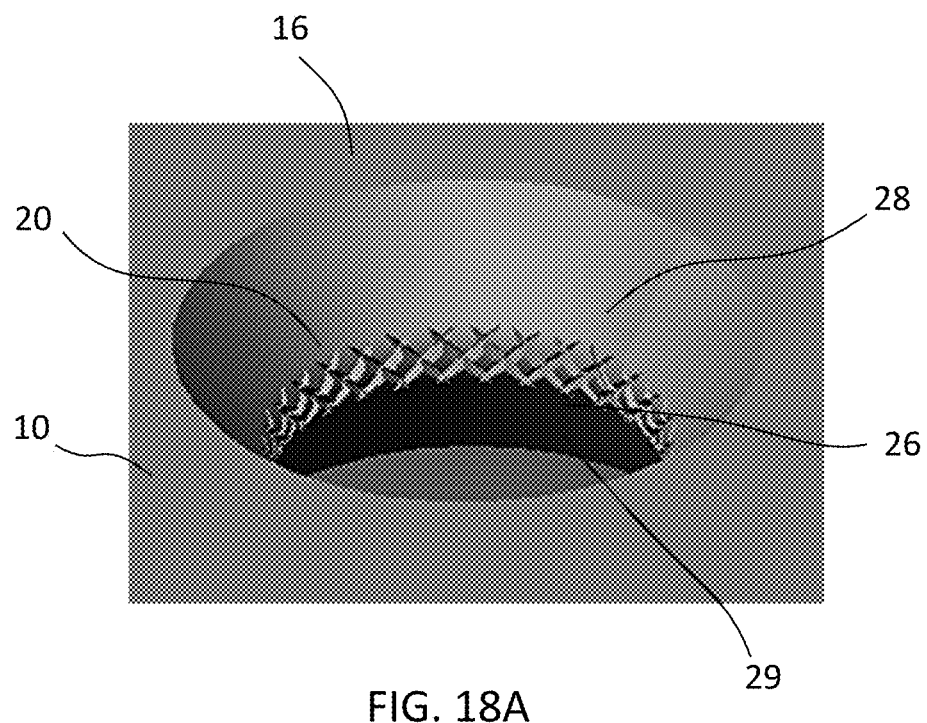
FIGS. 18A and 18B depict an opening in a plate according to another embodiment having a knurled cut configured to receive the self-forming threads of the fastener of FIGS. 16A-16B.
Figure 18B:
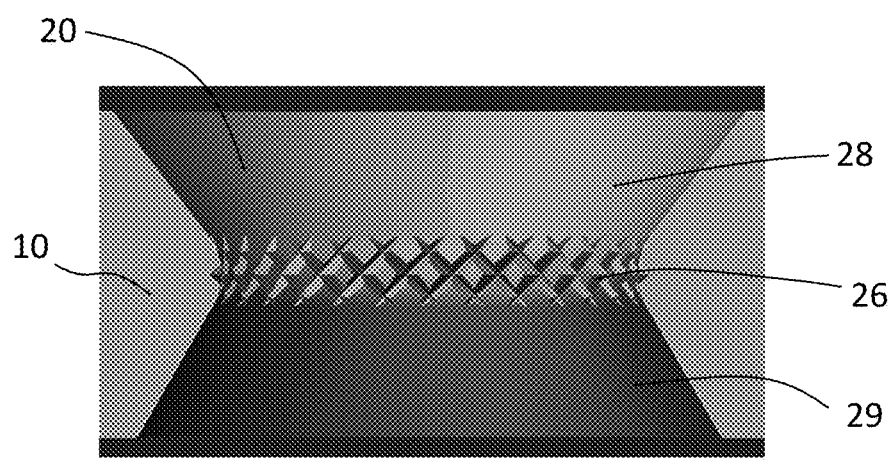
Figure 19A:
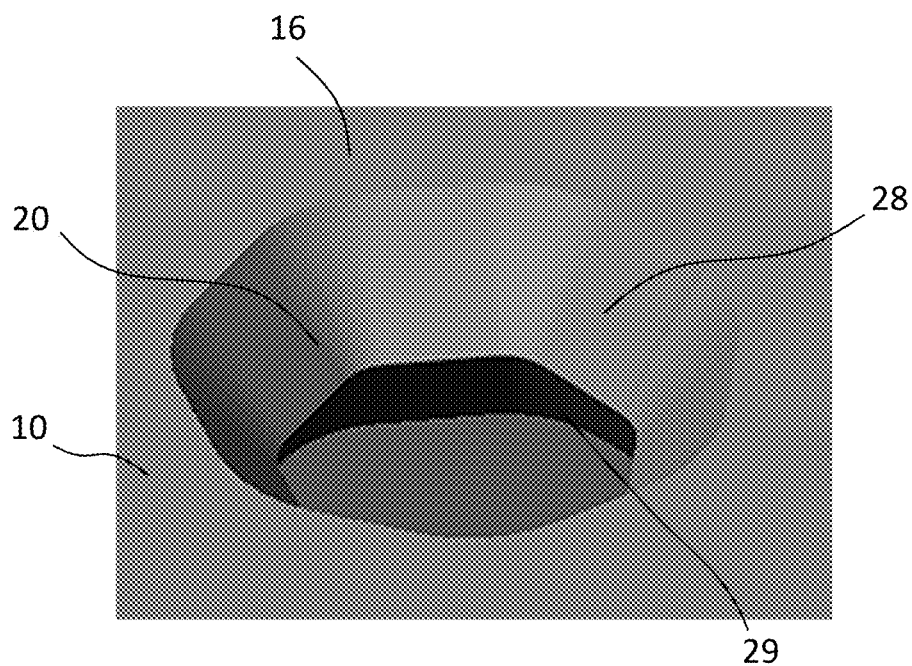
FIGS. 19A and 19B depict an opening in a plate according to another embodiment having a polygonal cut configured to receive the self-forming threads of the fastener of FIGS. 16A-16B.
Figure 19B:
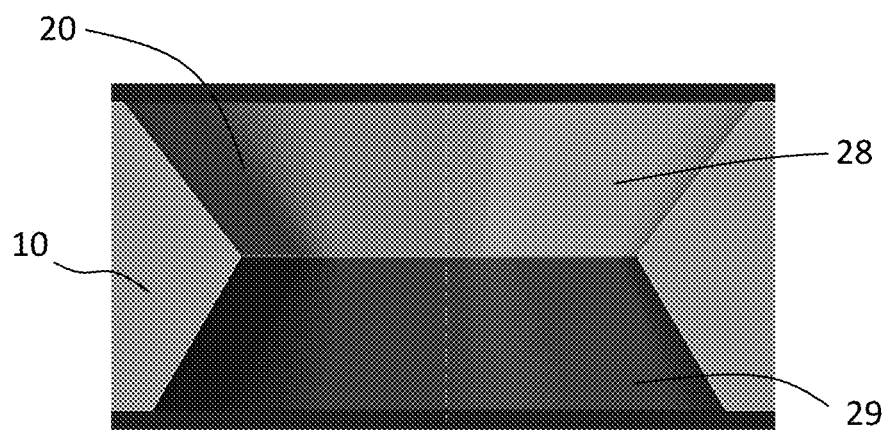

In FIGS. 18A-18B, the textured portion 26 includes a knurled cut design. A rounded transition between the upper tapered portion 28 and the lower tapered portion 29 (e.g., the two conical cuts) provides a workable surface for the knurling process as well as a surface for the head portion 32 to be able to roll over during off-axis locking. The knurled design may include a plurality of shallow knurled grooves set in a diamond pattern (e.g., about 45°) where each cut overlaps the next. The knurled grooves allow for the self-forming threads to cut more deeply into the material and reduce the necessary axial force to begin the thread forming process. FIGS. 19A-19B depict a polygon form cut design. In this design, there is no textured portion at the transition between the upper tapered portion 28 and the lower tapered portion 29. Instead, the narrowed central region has an overall polygonal form such that the hole 20 is neither cylindrical nor conical. The polygonal shape includes a number of sides with distinct linear section of material and rounded corners around which the form cut is allowed to sweep. For example, the polygonal shape may be substantially hexagonal (6-sided), heptagonal (7-sided), octagonal (8-sided), etc. The hole 20 may also be represented without lobe cuts, as a single concentric ring with the same geometry.

Figure 20A:
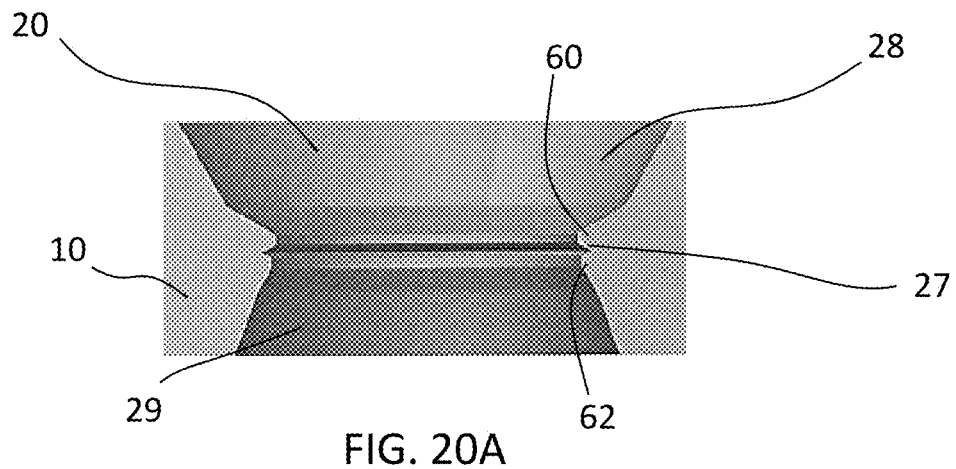
FIG. 20A depicts an alternative opening in a plate according to another embodiment.

In FIG. 20A, the upper tapered portion 28 includes a conical straight tapered surface cut for clearance of the head portion 32 of the fastener 30 during off angle insertion. The upper tapered portion 28 is segmented to have an upper area with a larger area relative to a lower area proximate the transition to the lower tapered portion 29 having a narrower diameter. The central area between the upper and lower tapered portions 28, 29, where the thread forming process occurs, includes two peaks or concentric rings of material (e.g., a superficial ring 60 and a deep ring 62) with a groove 27 being locating in between for material removal and thread forming relief. The groove 27 between the rings 60, 62 may be angled, for example, in the range of about 40-80°, about 50-70°, or about 60°. The superficial ring 60 is of a slightly smaller inner diameter than the deep ring 62, as the superficial ring 60 is responsible for supporting a majority of the cantilever loads. The deep ring 62 provides additional fixation and support during off-angle insertion as well as additional support during nominal trajectory insertion. The lower tapered portion 29 includes a straight tapered surface that provides clearance for the shaft 34 of the fastener 30 when inserted off angle.

Figure 20B:
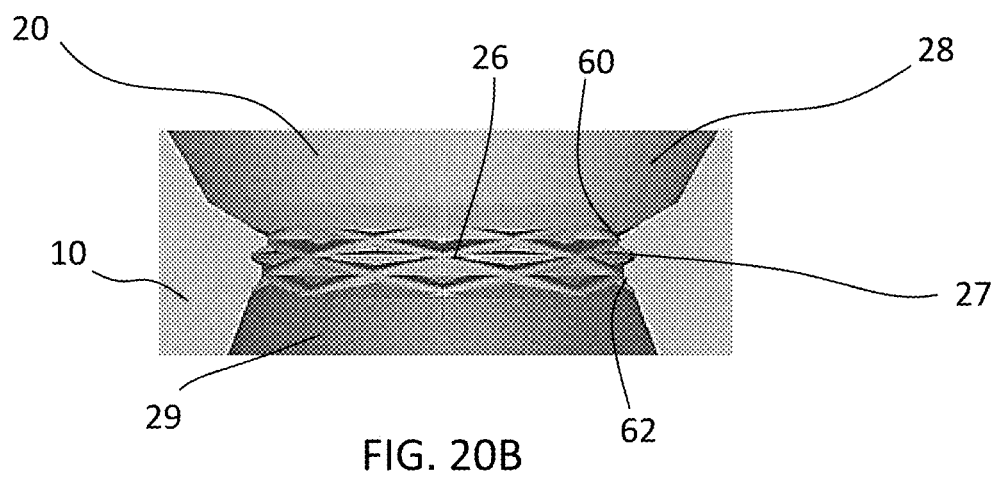
FIG. 20B depicts another alternative opening in a plate according to yet another embodiment.

The embodiment of the opening 20 in FIG. 20B is similar to FIG. 20A, but further includes textured portion 26 in the form of a plurality of helical swept cuts at the transition between the upper tapered portion 28 and the lower tapered portion 29. The shallow helical cuts or windswept cuts may include a series of cuts at a steep pitch. The windswept cuts may be angled, for example, at about 50-70°, or about 60°. The same number of cuts may be made in both a clockwise and counter-clockwise fashion. The cuts may create plateaus of material protruding into the opening 20. The resultant geometry provides positive surfaces for the fastener 30 to cut into, which can dramatically reduce the axial force necessary to lock the fastener 30 to the plate 10. Thus mechanism does not need to rely on bone purchase in order to engage the threads in the head portion 32 of the fastener 30. The material removed during insertion of the fastener 30 allows the self-forming threads to cut deeper by removing material which much be formed and reducing friction between the fastener 30 and the plate 10 during the forming process.

Figure 21A:
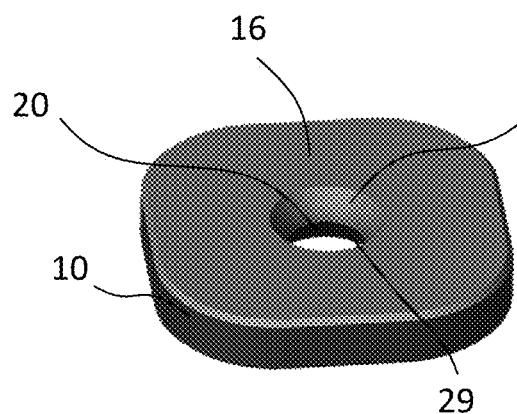
FIGS. 21A-21D depict a plate assembly according to one embodiment where a locking or non-locking fastener may be positioned at an angle or perpendicular to the plate.
Figure 21B:
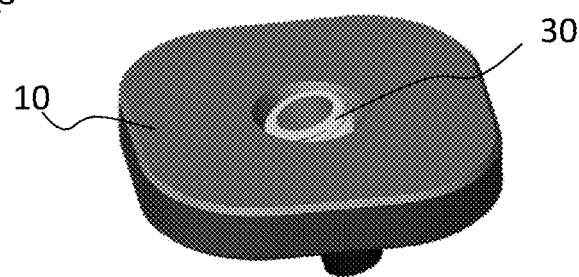
Figure 21C:
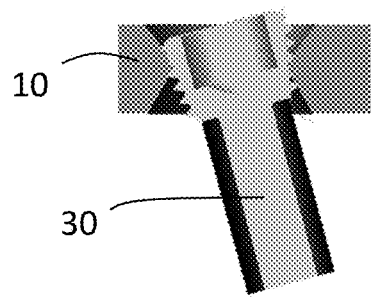
Figure 21D:
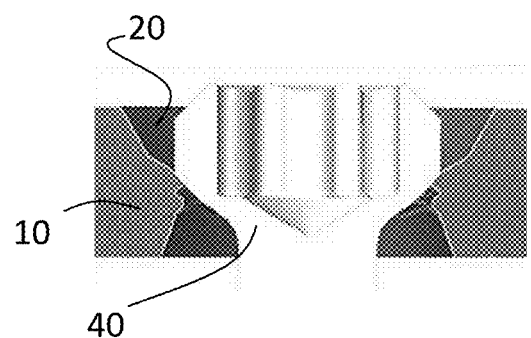

FIGS. 21A-21D depict a screw-plate assembly. The assembly, in FIG. 21C, shows the locking fastener 30 placed at an angle, other than perpendicular, to the upper surface 16 of the plate 10. In FIG. 21D, a non-locking fastener 40 is placed generally perpendicular to the plate 10. It will be appreciated that the locking fastener 30 and non-locking fastener 40 may be oriented at any appropriate angle relative to the plate 10. The section view in FIG. 21C shows the thread engagement with the plate 10 in which material of the plate 10 is displaced around the threads of the fastener 30. By using the self-forming threads, the fastener 30 is able to be inserted into the plate 10 at variable angles and engages with the plate 10 with one-step locking requiring no additional steps to lock the fastener 30 to the plate 10. The section view in FIG. 21D show the compressive, non-locking screw 40 received in the opening 20, without threadedly locking thereto. The non-locking screw 40 may provide for dynamic compression of the bone. Accordingly, the fasteners and openings described herein provide a wide variety of options for the surgeon, thereby providing appropriate locking and/or unlocking capability for dynamic compression depending on the desired treatment of the fracture and the bone.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A stabilization system for stabilizing a bone, the system comprising:
a bone plate, the bone plate comprising an elongated portion extending along a longitudinal axis and an enlarged head portion extending from the elongated portion, the bone plate comprising a plurality of through holes;
an intramedullary nail, the intramedullary nail comprising an upper portion and a lower portion extending from the upper portion, the upper portion and the lower portion including a plurality of holes; and
a plurality of fasteners configured to extend through the plurality of through holes in the bone plate and through the plurality of holes in the intramedullary nail and into the bone such that the plurality of fasteners are oriented obliquely with respect to each other,
wherein the enlarged head portion extends at a lateral angle relative to the longitudinal axis,
wherein the plurality of through holes have an upper portion and a lower portion, the upper portion is tapered with a conical straight tapered surface cut through a top surface of the bone plate, and the lower portion is tapered with a conical surface, wherein the upper portion and the lower portion have different conical sections having different degrees of taper.

2. The stabilization system of claim 1, wherein the plurality of through holes comprise first and second polyaxial openings, and the plurality of fasteners comprise polyaxial calcar screws configured to be received in the first and second polyaxial openings and configured to be aimed at a calcar region of a proximal humerus.

3. The stabilization system of claim 1, wherein the plurality of through holes comprise a plurality of fixed angle openings positioned on the enlarged head portion of the plate, and the plurality of fasteners comprise fixed angle, locking screws configured to be received in the respective fixed angle openings and the upper portion of the intramedullary nail and configured to be aimed at a humeral head.

4. The stabilization system of claim 1, wherein the plurality of through holes comprise a plurality of elongated slots positioned on the elongated portion of the plate, and the plurality of fasteners comprise at least one polyaxial screw configured to be received in at least one of the plurality of elongated slots and within one of the plurality of holes in the lower portion of the intramedullary nail to permit dynamic compression of the bone.

5. The stabilization system of claim 1, wherein the plurality of fasteners include fasteners having self-forming threads on a head portion of the fasteners, which are configured to lock to at least one of the plurality of through holes on the plate.

6. The stabilization system of claim 1, wherein the lower portion of the intramedullary nail is configured to be positioned in an intramedullary canal and the upper portion of the intramedullary nail is configured to be positioned in a humeral head.

7. The stabilization system of claim 1, wherein the plate further comprises a second plurality of openings configured as suture holes to receive sutures configured to secure the plate to surrounding tissue.

8. The stabilization system of claim 1, wherein the lower portion is fixed in position relative to the upper portion of the intramedullary nail.

9. The stabilization system of claim 1, wherein the plate has a length greater than a length of the intramedullary nail.

10. A stabilization system for stabilizing a bone, the system comprising:
 a bone plate, the bone plate comprising an elongated portion extending along a longitudinal axis and an enlarged head portion extending from the elongated portion, the bone plate comprising a plurality of through holes through the enlarged head portion and the elongated portion;
 an intramedullary nail, the intramedullary nail comprising an upper portion and a lower portion extending from the upper portion, the upper portion and the lower portion including a plurality of holes;
 a first plurality of fasteners positioned through the plurality of through holes in the enlarged head portion of the bone plate and through the plurality of holes in the upper portion of the intramedullary nail and into the bone such that the plurality of fasteners are oriented obliquely with respect to each other;
 a second plurality of fasteners positioned through the plurality of through holes in the elongated portion of the bone plate and through the plurality of holes in the lower portion of the intramedullary nail and into the bone;
 a third plurality of fasteners positioned through the plurality of through holes in the bone plate and directly into bone without passing through the intramedullary nail,
 wherein the enlarged head portion extends at a lateral angle relative to the longitudinal axis,
 wherein the plurality of through holes have an upper portion and a lower portion, the upper portion is tapered with a conical straight tapered surface cut through a top surface of the bone plate, and the lower portion is tapered with a conical surface, wherein the upper portion and the lower portion have different conical sections having different degrees of taper.

11. The stabilization system of claim 10, further comprising a single fastener positioned through one of the plurality of through holes in the elongated portion of the bone plate and directly into bone without passing through the intramedullary nail.

12. The stabilization system of claim 10, wherein the plurality of through holes comprise first and second polyaxial openings, and the first plurality of fasteners comprise polyaxial calcar screws configured to be received in the first and second polyaxial openings and configured to be aimed at a calcar region of a proximal humerus.

13. The stabilization system of claim 10, wherein the plurality of through holes comprise a plurality of fixed angle openings positioned on the enlarged head portion of the plate, and the first plurality of fasteners comprise fixed angle, locking screws configured to be received in the respective fixed angle openings and the upper portion of the intramedullary nail and configured to be aimed at a humeral head.

14. The stabilization system of claim 10, wherein the plurality of through holes comprise a plurality of elongated slots positioned on the elongated portion of the plate, and the second plurality of fasteners comprise at least one polyaxial screw configured to be received in at least one of the plurality of elongated slots and within one of the plurality of holes in the lower portion of the intramedullary nail to permit dynamic compression of the bone.

15. The stabilization system of claim 10, wherein the first, second, or third plurality of fasteners include fasteners having self-forming threads on a head portion of the fasteners, which are configured to lock to at least one of the plurality of through holes on the plate.

16. The stabilization system of claim 10, wherein the lower portion of the intramedullary nail is configured to be positioned in an intramedullary canal and the upper portion of the intramedullary nail is configured to be positioned in a humeral head.

17. The stabilization system of claim 10, wherein the plate further comprises a second plurality of openings configured as suture holes to receive sutures configured to secure the plate to surrounding tissue.

\* \* \* \* \*